United States Patent
Passno et al.

(10) Patent No.: US 11,358,984 B2
(45) Date of Patent: Jun. 14, 2022

(54) USE OF RAMAN SPECTROSCOPY IN DOWNSTREAM PURIFICATION

(71) Applicant: Regeneron Pharmaceuticals, Inc., Tarrytown, NY (US)

(72) Inventors: Christina Passno, Allendale, NJ (US); Christopher Cowan, Ossining, NY (US); Andrew Tustian, Millwood, NY (US)

(73) Assignee: Regeneran Pharmaceuticals, Inc., Tarrytown, NY (US)

( * ) Notice: Subject to any disclaimer, the term of this patent is extended or adjusted under 35 U.S.C. 154(b) by 226 days.

(21) Appl. No.: 16/550,989

(22) Filed: Aug. 26, 2019

(65) Prior Publication Data
US 2020/0062802 A1  Feb. 27, 2020

Related U.S. Application Data

(60) Provisional application No. 62/723,188, filed on Aug. 27, 2018.

(51) Int. Cl.
*C07K 1/14* (2006.01)
*C07K 1/34* (2006.01)
(Continued)

(52) U.S. Cl.
CPC ............. *C07K 1/36* (2013.01); *C07K 1/145* (2013.01); *C07K 1/34* (2013.01); *G01N 1/4044* (2013.01);
(Continued)

(58) Field of Classification Search
CPC . C07K 1/145; C07K 1/34; C07K 1/36; C07K 16/00; G01N 1/4044; G01N 1/4077; G01N 2001/4088; G01N 21/65
See application file for complete search history.

(56) References Cited

U.S. PATENT DOCUMENTS 5,675,931 A   10/1997 Wasserman
6,156,570 A   12/2000 Hu et al.
(Continued)

FOREIGN PATENT DOCUMENTS

AR       113449 A1    5/2020
AU    2018350890 A1   3/2020
(Continued)

OTHER PUBLICATIONS

Li et al., "Rapid Characterization and Quality Control of Complex Cell Culture Media Solutions Using Raman Spectroscopy and Chemometrics," Biotech. Bioengineer, vol. 107, No. 2: 290-301, (Year: 2010).
(Continued)

*Primary Examiner* — Jennifer Wecker
(74) *Attorney, Agent, or Firm* — McCarter & English, LLP; John P. Isacson

(57) ABSTRACT

In situ Raman spectroscopy methods and systems for characterizing or quantifying a protein purification intermediate and/or final concentrated pool during production or manufacture are provided. In one embodiment, in situ Raman spectroscopy is used to characterize or quantify protein purification intermediates critical quality attributes during downstream processing (i.e., after harvest of the protein purification intermediate). For example, the disclosed in situ Raman spectroscopy methods and systems can be used to characterize and quantify protein purification intermediates as the protein purification intermediates are purified, condensed, or otherwise formulated into the final drug product to be sold or administered.

41 Claims, 20 Drawing Sheets

(51) Int. Cl.
*G01N 1/40* (2006.01)
*G01N 21/65* (2006.01)
*C07K 1/36* (2006.01)

(52) U.S. Cl.
CPC ........... *G01N 1/4077* (2013.01); *G01N 21/65* (2013.01); *G01N 2001/4088* (2013.01)

(56) References Cited

U.S. PATENT DOCUMENTS

| | | |
|---|---|---|
| 6,939,686 B2 | 9/2005 | Ling et al. |
| 7,221,457 B2 | 5/2007 | Jorgenson et al. |
| 7,429,491 B2 | 9/2008 | Luan et al. |
| 7,843,562 B2 | 11/2010 | Chan et al. |
| 8,243,267 B2 | 8/2012 | Siegel et al. |
| 8,318,416 B2 | 11/2012 | Tsang et al. |
| 8,325,339 B2 | 12/2012 | Ebstein |
| 8,477,307 B1 | 7/2013 | Yufa et al. |
| 8,547,550 B2 | 10/2013 | Carpenter |
| 9,212,379 B2 | 12/2015 | Tsang et al. |
| 9,290,568 B2 | 3/2016 | Rives et al. |
| 9,365,883 B2 | 6/2016 | Gannot et al. |
| 9,388,373 B2 | 7/2016 | Rao et al. |
| 9,506,867 B2 | 11/2016 | Moretto et al. |
| 9,829,437 B2 | 11/2017 | Chau et al. |
| 9,856,505 B2 | 1/2018 | Bartko |
| 9,879,299 B2 | 1/2018 | Yamakawa et al. |
| 10,067,051 B2 | 9/2018 | Diem et al. |
| 10,101,209 B2 | 10/2018 | Selker et al. |
| 10,261,020 B2 | 4/2019 | Tedesco et al. |
| 10,338,078 B2 | 7/2019 | Sodeoka et al. |
| 10,548,517 B2 | 2/2020 | Cho et al. |
| 10,563,163 B2 | 2/2020 | Berry et al. |
| 10,774,304 B2 | 9/2020 | Rao et al. |
| 10,918,319 B2 | 2/2021 | Lee et al. |
| 2004/0057040 A1 | 3/2004 | Beckenkamp et al. |
| 2006/0281068 A1 | 12/2006 | Maier et al. |
| 2010/0136609 A1 | 6/2010 | Clay et al. |
| 2010/0256336 A1 | 10/2010 | Yuk et al. |
| 2010/0291599 A1 | 11/2010 | Tague, Jr. et al. |
| 2011/0081672 A1 | 4/2011 | Andersen et al. |
| 2012/0122076 A1* | 5/2012 | Lau ................. C07K 1/14 435/4 |
| 2012/0123688 A1* | 5/2012 | Ramasubramanyan ................. G01N 33/6854 702/19 |
| 2012/0275681 A1 | 11/2012 | Honda et al. |
| 2013/0177972 A1 | 7/2013 | Green et al. |
| 2015/0110799 A1* | 4/2015 | Ramasubramanyan ................. A61K 47/26 424/142.1 |
| 2015/0247210 A1 | 9/2015 | Olesberg et al. |
| 2016/0025633 A1 | 1/2016 | Moretto et al. |
| 2016/0069809 A1 | 3/2016 | Bonnier et al. |
| 2016/0103072 A1 | 4/2016 | Fukutake et al. |
| 2016/0341667 A1 | 11/2016 | Ramasubramanyan et al. |
| 2017/0355947 A9 | 12/2017 | Berry et al. |
| 2018/0020956 A1 | 1/2018 | Lee et al. |
| 2018/0023111 A1 | 1/2018 | Schutze et al. |
| 2018/0149597 A1 | 5/2018 | Umezaki et al. |
| 2018/0180549 A1 | 6/2018 | Lewis |
| 2018/0261329 A1 | 9/2018 | Blander et al. |
| 2018/0291329 A1* | 10/2018 | Moretto ............. C07K 16/06 |
| 2018/0292324 A1 | 10/2018 | Verma et al. |
| 2019/0112569 A1* | 4/2019 | Czeterko ............. C12M 41/32 |
| 2019/0137338 A1 | 5/2019 | Webster et al. |
| 2019/0153381 A1 | 5/2019 | Angelini et al. |
| 2019/0376020 A1 | 12/2019 | Bickham et al. |
| 2020/0096448 A1 | 3/2020 | Gillner et al. |
| 2020/0116638 A1 | 4/2020 | Duraipandian et al. |
| 2020/0150022 A1 | 5/2020 | Ugawa et al. |
| 2020/0200763 A1 | 6/2020 | Min et al. |
| 2020/0239852 A1 | 7/2020 | Hiller et al. |
| 2020/0283713 A1 | 9/2020 | Ball et al. |
| 2020/0292538 A1 | 9/2020 | Olivo et al. |
| 2020/0392447 A1 | 12/2020 | Berry et al. |
| 2021/0009935 A1 | 1/2021 | Saito et al. |
| 2021/0017553 A1 | 1/2021 | Hiller et al. |
| 2021/0024872 A1 | 1/2021 | Martin et al. |
| 2021/0025814 A1 | 1/2021 | Stacey et al. |
| 2021/0040431 A1 | 2/2021 | Mogi |
| 2021/0047606 A1 | 2/2021 | Ray et al. |
| 2021/0062133 A1 | 3/2021 | Hassell et al. |
| 2021/0094982 A1 | 4/2021 | Ludemann-Hombourger et al. |

FOREIGN PATENT DOCUMENTS

| | | |
|---|---|---|
| CA | 2882003 A1 | 2/2014 |
| CA | 3078956 A1 | 4/2019 |
| CN | 101482509 A | 7/2009 |
| CN | 101482554 A | 7/2009 |
| CN | 104297225 A | 1/2015 |
| CN | 104774756 A | 7/2015 |
| CN | 105738343 A | 7/2016 |
| CN | 106295251 A | 1/2017 |
| CN | 106645079 A | 5/2017 |
| CN | 106769693 A | 5/2017 |
| CN | 108037107 A | 5/2018 |
| CN | 108169203 A | 6/2018 |
| CN | 108267437 A | 7/2018 |
| CN | 108459001 A | 8/2018 |
| CN | 109266717 A | 1/2019 |
| CN | 109342393 A | 2/2019 |
| CN | 109342403 A | 2/2019 |
| CN | 110208238 A | 9/2019 |
| CN | 209460143 U | 10/2019 |
| CN | 110441287 A | 11/2019 |
| CN | 110501319 A | 11/2019 |
| CN | 110646401 A | 1/2020 |
| CN | 111201434 A | 5/2020 |
| CN | 111220589 A | 6/2020 |
| CN | 111220590 A | 6/2020 |
| CN | 111289489 A | 6/2020 |
| CN | 111433592 A | 7/2020 |
| CN | 111912826 A | 11/2020 |
| CN | 112014372 A | 12/2020 |
| DE | 10217948 A1 | 11/2003 |
| EP | 3380825 A1 | 10/2018 |
| EP | 3611495 A1 | 2/2020 |
| EP | 3709005 A1 | 9/2020 |
| JP | 2020-532993 A | 11/2020 |
| JP | 2020-536497 A | 12/2020 |
| JP | 2020-536521 A | 12/2020 |
| JP | 2020-537126 A | 12/2020 |
| JP | 2021-048872 A | 4/2021 |
| KR | 10-2018-0059739 A | 6/2018 |
| KR | 10-2019-0054746 A | 5/2019 |
| KR | 10-2020-0070218 A | 6/2020 |
| SG | 1120201127 T | 3/2020 |
| TW | 201928042 A | 7/2019 |
| TW | 202033949 A | 9/2020 |
| WO | 1997/036540 A1 | 10/1997 |
| WO | WO-2012/037430 A1 | 3/2012 |
| WO | WO-2012/040041 A1 | 3/2012 |
| WO | 2014/137291 A1 | 9/2014 |
| WO | 2014/170684 A1 | 10/2014 |
| WO | 2015/095255 A1 | 6/2015 |
| WO | WO-2015/145149 A1 | 10/2015 |
| WO | 2016/004322 A2 | 1/2016 |
| WO | 2016/196315 A2 | 12/2016 |
| WO | 2017/164815 A1 | 9/2017 |
| WO | 2018/031954 A1 | 2/2018 |
| WO | 2018/159833 A1 | 9/2018 |
| WO | 2018/188395 A1 | 10/2018 |
| WO | 2019/062689 A1 | 4/2019 |
| WO | 2019/079165 A1 | 4/2019 |
| WO | 2019/117177 A1 | 6/2019 |
| WO | 2019/157263 A1 | 8/2019 |
| WO | 2019/185860 A1 | 10/2019 |
| WO | 2019/211531 A1 | 11/2019 |
| WO | 2020/007326 A1 | 1/2020 |
| WO | 2020/037117 A1 | 2/2020 |
| WO | 2020/086635 A1 | 4/2020 |
| WO | 2020/087040 A1 | 4/2020 |

(56) References Cited

FOREIGN PATENT DOCUMENTS

| WO | 2020/090225 | A1 | 5/2020 |
|---|---|---|---|
| WO | 2020/124271 | A1 | 6/2020 |
| WO | 2020/162601 | A1 | 8/2020 |
| WO | 2020/180003 | A1 | 9/2020 |
| WO | 2020/186026 | A1 | 9/2020 |
| WO | 2020/227571 | A1 | 11/2020 |
| WO | 2020/237221 | A1 | 11/2020 |
| WO | 2020/238918 | A1 | 12/2020 |
| WO | 2020/247952 | A2 | 12/2020 |
| WO | 2020/260073 | A1 | 12/2020 |
| WO | 2020/260229 | A1 | 12/2020 |
| WO | 2021/026172 | A1 | 2/2021 |
| WO | 2021/030672 | A1 | 2/2021 |

OTHER PUBLICATIONS

Abu-Absi, et al., "Real Time Monitoring of Multiple Parameters in Mammalian Cell Culture Bioreactors Using an In-Line Raman Spectroscopy Probe," Biotechnol Bioeng, 108(5):1215-1221 (2011).

Ashton, L., et al., "The challenge of applying Raman spectroscopy to monitor recombinant antibody production," Analyst, 138:6977-6985 (2013).

Carey PR. "Biochemical Applications of Raman and Resonance Raman Spectroscopies", New York: Academic Press (1982).

Haberger, M., et al. "Assessment of chemical modifications of sites in the CDRs of recombinant antibodies" MAbs. 6:327-339 (2014).

Harada I. Miura T, Takeuchi H. "Origin of the doublet at 1360 and 1340 cmS1 in the Raman spectra of tryptophan and related compounds". Spectrochim Acta A 42:307-312 (1986).

Hodge JE, "Chemistry of Browning Reactions in Model Systems" J Agric Food Chem. 1:928-943 (1953).

Lewis, N. et al, "Combined Dynamic Light Scattering and Raman Spectroscopy Approach for Characterizing the Aggregation of Therapeutic Proteins", Molecules, 19(12), 20888-20905 (2014).

Li H, Thomas GJ Jr. "Cysteine conformation and sulfhydryl interactions in proteins and viruses. 1. Correlation of the Raman S-H band with hydrogen bonding and intramolecular geometry in model compounds" J Am Chem Soc 113:456-462 (1991).

Li H, Wurrey CJ, Thomas GJ Jr. "Cysteine conformation and sulfhydryl interactions in proteins and viruses. 2. Normal coordinate analysis of the cysteine side chain in model compounds", J Am Chem Soc 114:7463-7469 (1992).

Milligan, M., et al., "Semisynthetic model calibration for monitoring glucose in mammalian cell culture with in situ near infrared spectroscopy", Biotechnol Bioeng, 111(5): 896-903 (2014).

Miura T, Takeuchi H, Harada I. Tryptophan Raman bands sensitive to hydrogen bonding and side chain conformation. J Raman Spectrosc 20:667-671 (1989).

Mungikar, A., Kamat M.. "Use of In-line Raman Spectroscopy as a Non-destructive and Rapid Analytical Technique to Monitor Aggregation of a Therapeutic Protein", American Pharmaceutical Review (2010).

Schwartz, L. Diafiltration: A Fast, Efficient Method for Desalting, or Buffer Exchange of Biological Samples. Scientific & Technical Report PN 33289, Pall Life Sciences.

Stoner MR, et al. Protein-solute interactions affect the outcome of ultrafiltration/diafiltration operations. J Pharm Sci. 93(9):2332-2342 (2004).

Sugeta H, Go A, Miyazawa T. "Vibrational spectra and molecular conformations of dialkyl disulfides", Bull Chem Soc Jpn 46:3407-3411 (1973).

Sugeta H.. "Normal vibrations and molecular conformations of dialky disulfides", Spectrochim Acta 31A:1729-1737 (1975).

Van Wart HE, et al. "Disulfide bond dihedral angles from Raman spectroscopy", Proc Natl Acad Sci USA 70:2617-2623 (1973).

Van Wart H, Scheraga HA. "Agreement with the disulfide stretching frequency-conformation correlation of Sugeta. Go and Miyazawa", Proc Natl Acad Sci USA 83: 3064-3067 (1986).

Wen ZQ, Thomas GJ Jr. "Ultraviolet resonance Raman spectroscopy of the filamentous virus Pf3: interaction of Trp 38 specific to the assembled virion subunit." Biochemistry 39:146-152 (2000).

Wen, ZQ. "Raman Spectroscopy of Protein Pharmaceuticals." Journal of Pharmaceutical Sciences, vol. 96, No. 11 (2007).

Wen, Z., Cao, W., Phillips, J. Application of Raman Spectroscopy in Biopharmaceutical Manufacturing. American Pharmaceutical Review (Apr. May Jun. 2010).

Yuk, I.H., et al., "Controlling glycation of recombinant antibody fed-batch cell cultures," Biotechnol Bioeng, 108(11):2600-2610 (2011).

International Search Report and Written Opinion of the International Searching Authority, dated Nov. 20, 2019 (14 pages).

U.S. Appl. No. 16/160,194, filed Oct. 15, 2018, 2019-0112569, Published.

Buckley et al., Applications of Raman Spectroscopy in Biopharmaceutical Manufacturing: A Short Review. Appl Spectrosc. Jun. 2017;71(6):1085-1116.

Whelan et al., In situ Raman spectroscopy for simultaneous monitoring of multiple process parameters in mammalian cell culture bioreactors. Biotechnol Prog. Sep.-Oct. 2012;28(5):1355-62.

International Preliminary Report on Patentability for Application No. PCT/US2018/055837, dated Apr. 30, 2020, 7 pages.

International Search Report and Written Opinion for Application No. PCT/US2018/055837, dated Jan. 8, 2019, 9 pages.

Singapore Office Action for Application No. 11202001127T, dated Dec. 4, 2020, 11 pages.

\* cited by examiner

USE OF RAMAN SPECTROSCOPY IN DOWNSTREAM PURIFICATION

CROSS-REFERENCE TO RELATED APPLICATIONS

This application claims benefit of and priority to U.S. Provisional Patent Application No. 62/723,188 filed on Aug. 27, 2018, and where permissible is incorporated by reference in its entirety.

TECHNICAL FIELD OF THE INVENTION

The invention is generally directed to systems and methods for monitoring and controlling one or more critical quality attributes (CQAs) or parameters in downstream protein purification processes.

BACKGROUND OF THE INVENTION

The number of monoclonal antibodies (mAbs) that have been approved for therapeutic use has increased significantly over the past decade. This is due in part to improvements in large scale manufacturing processes which facilitate the production of large quantities of mAbs. In addition, initiatives such as The Process Analytical Technology (PAT) framework of the Food and Drug Administration (FDA) have led to innovative solutions to process development, process analysis, and process control to better understand processes and control the quality of products. Efficient recovery and purification of mAbs from cell culture media is a critical part of the production process. The purification process should reliably produce mAbs that are safe for use in humans. This includes monitoring critical quality attributes (CQAs) that include protein attributes and impurities such as host cell proteins, DNA, viruses, endotoxins, aggregates, concentrations, excipients, and other species that have the potential to impact patient safety, efficacy, or potency. Protein concentration is also often a CQA in purified material, and appropriate protein concentration in process intermediates can be a critical process parameter for unit operation performance. These CQAs need to be monitored throughout production as well as throughout the program lifecycle.

To ensure that the final formulations of mAbs do not contain impurities above determined levels, the mAb products are tested at various stages of the downstream processing. Quality control in the manufacturing of bioproducts such as mAbs is generally accomplished by analyzing purification intermediates and formulated drug substance samples with offline methods for each lot production. The samples are removed from the processing equipment, for example a UF/DF skid, and subjected to offline tests to measure product CQAs such as protein concentration (g/L), buffer excipients, and size variants. Real time monitoring and analysis during manufacturing is not available resulting in increases in processing time and a higher risk of batch failure due to not meeting CQAs. Accordingly, there is a need for rapid, in-line methods of real-time quality control monitoring of mAbs.

Therefore, it is an object of the invention to provide systems and methods for real-time monitoring of critical quality attributes during the downstream purification process.

SUMMARY OF THE INVENTION

In situ Raman spectroscopy methods and systems for characterizing or quantifying a protein purification intermediate during production or manufacture are provided. In one embodiment, in situ Raman spectroscopy is used to characterize or quantify critical quality attributes of a protein drug during downstream processing (i.e., after harvest of the protein purification intermediate from cell culture fluid). For example, the disclosed in situ Raman spectroscopy methods and systems can be used to characterize and quantify protein purification intermediate critical quality attributes as the protein purification intermediates are purified, prior to formulation into the final drug product to be sold or administered. Critical quality attributes include but are not limited to protein concentration, excipients, high molecular weight (HMW) species, antibody titer, and drug-antibody ratio.

One embodiment provides a method of producing a concentrated protein purification intermediate by determining concentrations of a protein purification intermediate in-real time using in situ Raman spectroscopy while concentrating/diafiltering the protein purification intermediate and adjusting parameters of the concentrating step in-real time to obtain the pre-determined concentration targets and excipient levels necessary for formulation of drug substance. The protein purification intermediate product can have a concentration of 5 mg/mL to 300 mg/mL, preferably 50 mg/mL to 300 mg/mL for subsequent formulation steps. In one embodiment, the protein purification intermediate is concentrated to a desired concentration target using ultrafiltration during primary or final concentration. Diafiltration is used during processing following primary concentration as a means for buffer exchange to achieve the desired final formulation components. The protein purification intermediate can be harvested from a bioreactor, a fed-batch culture, or a continuous culture. In another embodiment, determining the concentration of the protein purification intermediate can occur continuously or intermittently in real-time. Quantifying of protein concentration can be performed in intervals from approximately 5 seconds to 10 minutes, hourly, or daily. The protein purification intermediate can be an antibody or antigen binding fragment thereof, a fusion protein, or a recombinant protein. Spectral data can be collected at one or more wavenumber ranges selected from the group consisting of 977-1027 $cm^{-1}$, 1408-1485 $cm^{-1}$, 1621-1711 $cm^{-1}$, 2823-3046 $cm^{-1}$, and combinations thereof.

Another embodiment provides a method of producing a protein purification intermediate by independently performing Raman Spectroscopy analysis on a plurality of protein purification intermediates to produce a universal model capable of quantifying any one of the plurality of protein purification intermediates. The concentration of a protein purification intermediate can be determined using in situ Raman spectroscopy with the universal model during concentration of the protein purification intermediate from beginning to end of concentrating the protein purification intermediate. Another embodiment provides a method of producing a protein purification intermediate to produce a protein specific model capable of quantifying protein concentrations that would be used for commercial enabling productions of the protein.

The model can be produced using Partial Least Squares Regression Analysis of raw spectral data and using an orthogonal method for offline protein concentration data. Pre-processing techniques such as Standard Normal Variant (SNV) and/or point-smoothing technique can be $1^{st}$ derivative with 21 $cm^{-1}$ smoothing can be performed on the Raman spectroscopy data to dampen model variability and prediction error. Further model refinement can be performed to isolate spectral regions that correlate to CQA predictions such as protein concentration. In one embodiment, the model has ≤5% error margin, preferably ≤3% error margin.

Still another embodiment provides a method for monitoring and controlling the levels of excipients in harvested cell culture fluid and/or protein purification intermediate during downstream purification by determining concentrations of the excipients in-real time using in situ Raman spectroscopy while purifying the cell culture fluid or protein purification intermediate, and adjusting parameters of the purification step in-real time to obtain or maintain predetermined amounts of the excipients in the harvested cell culture fluid and/or protein purification intermediate. The excipient can be acetate, citrate, histidine, succinate, phosphate, hydroxymethylaminomethane (Tris), proline, arginine, sucrose, or combinations thereof. The excipient can be a surface excipient such as polysorbate 80, polysorbate 20, and poloxamer 188.

BRIEF DESCRIPTION OF THE DRAWINGS

FIG. 8A shows the Raman model error for real-time predictions in various stages of UF/DF processing (primary concentration, diafiltration, and final concentrated pool). FIG. 8B shows the Raman model error for the final DoE model at various stages of UF/DF processing (primary concentration, diafiltration, and final concentrated pool).

DETAILED DESCRIPTION OF THE INVENTION

I. Definitions

Figure 1:
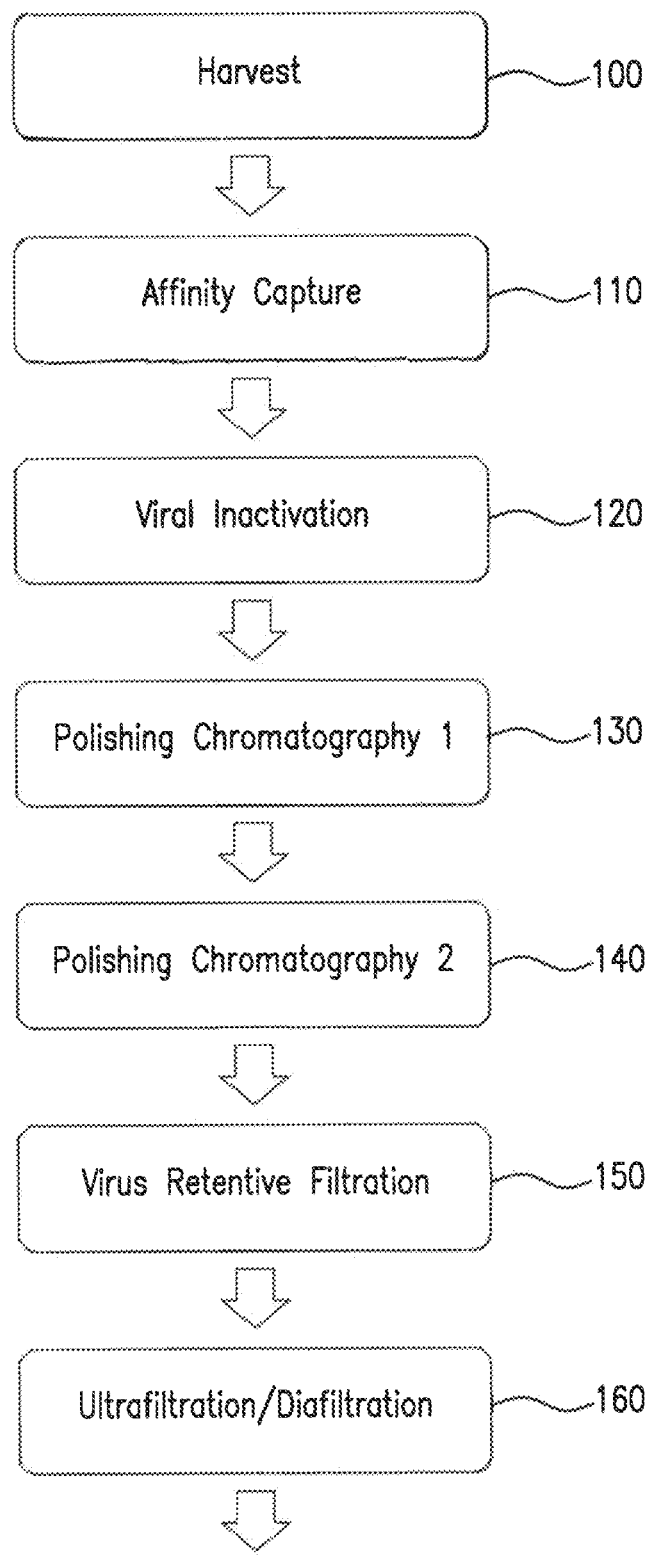
FIG. 1 is a flow chart showing an exemplary protein purification process.

It should be appreciated that this disclosure is not limited to the compositions and methods described herein as well as the experimental conditions described, as such may vary. It is also to be understood that the terminology used herein is for the purpose of describing certain embodiments only, and is not intended to be limiting, since the scope of the present disclosure will be limited only by the appended claims.

Unless defined otherwise, all technical and scientific terms used herein have the same meaning as commonly understood by one of ordinary skill in the art to which this disclosure belongs. Although any compositions, methods and materials similar or equivalent to those described herein can be used in the practice or testing of the present invention. All publications mentioned are incorporated herein by reference in their entirety.

The use of the terms "a," "an," "the," and similar referents in the context of describing the presently claimed invention (especially in the context of the claims) are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein.

Use of the term "about" is intended to describe values either above or below the stated value in a range of approx. ±10%; in other embodiments the values may range in value either above or below the stated value in a range of approx. ±5%; in other embodiments the values may range in value either above or below the stated value in a range of approx. ±2%; in other embodiments the values may range in value either above or below the stated value in a range of approx. ±1%. The preceding ranges are intended to be made clear by context, and no further limitation is implied. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, "protein" refers to a molecule comprising two or more amino acid residues joined to each other by a peptide bond. Protein includes polypeptides and peptides and may also include modifications such as glycosylation, lipid attachment, sulfation, gamma-carboxylation of glutamic acid residues, alkylation, hydroxylation and ADP-ribosylation. Proteins can be of scientific or commercial interest, including protein-based drugs, and proteins include, among other things, enzymes, ligands, receptors, antibodies and chimeric or fusion proteins. Proteins are produced by various types of recombinant cells using well-known cell culture methods, and are generally introduced into the cell by transfection of genetically engineering nucleotide vectors (e.g., such as a sequence encoding a chimeric protein, or a codon-optimized sequence, an intronless sequence, etc.), where the vectors may reside as an episome or be integrated into the genome of the cell.

"Antibody" refers to an immunoglobulin molecule consisting of four polypeptide chains, two heavy (H) chains and two light (L) chains inter-connected by disulfide bonds. Each heavy chain has a heavy chain variable region (HCVR or VH) and a heavy chain constant region. The heavy chain constant region contains three domains, CH1, CH2 and CH3. Each light chain has a light chain variable region and a light chain constant region. The light chain constant region consists of one domain (CL). The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. The term "antibody" includes reference to both glycosylated and non-glycosylated immunoglobulins of any isotype or subclass. The term "antibody" includes antibody molecules prepared, expressed, created or isolated by recombinant means, such as antibodies isolated from a host cell transfected to express the antibody. The term antibody also includes bispecific antibody, which includes a heterotetrameric immunoglobulin that can bind to more than one different epitope. Bispecific antibodies are generally described in US Patent Application Publication No. 2010/0331527, which is incorporated by reference into this application.

"Secondary structure" refers to local folded structures that form within a polypeptide due to interactions between atoms of the backbone. The most common types of secondary structures are α helix and the β pleated sheet. Both structures are held in shape by hydrogen bonds, which form between the carbonyl O of one amino acid and the amino H of another.

As used herein, "excipient" refers to a pharmacologically inactive substance that is used as a stabilizing agent for long-term storage of the formulated drug substance. Generally, additional excipients are added to the final concentrated pool to produce formulated drug substance. However, during UF/DF processing excipient levels are monitored to ensure the levels will not impact the desired formulation strategy. Excipients provide bulk to the pharmaceutical formulation, facilitate drug absorption or solubility, and provide stability and prevent denaturation. Common pharmaceutical excipients include but are not limited to amino acids, fillers, binders, disintegrants, coatings, sorbents, buffering agents, chelating agents, lubricants, glidants, preservatives, antioxidants, flavoring agents, sweeteners, coloring agents, solvent and co-solvents, and viscosity imparting agents. In one embodiment, the excipient is polyethylene glycol including but not limited to PEG-3550.

"Polyethylene glycol" or "PEG" is a polyether polymer of ethylene oxide commonly used in food, medicine and cosmetics. It is a non-ionic macromolecule that is useful as a molecule that reduces the solubility of a biomolecule. PEG is commercially available in different molecular weights ranging from 300 g/mol to 10,000,000 g/mol. Exemplary types of PEG include but are not limited to PEG 20000, PEG 8000 and PEG 3350. PEG is available in different geometries, including linear, branched (3-10 chains attached to central core), star-shaped (10-100 chains attached to a central core), and combshaped (multiple chains attached to a polymer backbone).

"Raman spectroscopy" is a spectroscopic technique used to measure the wavelength and intensity of in-elastically scattered light from molecules. It is based on the principle that monochromatic incident radiation on materials will be reflected, absorbed, or scattered in a specific manner, which is dependent upon the particular molecule or protein which receives the radiation. The majority of the energy is scattered at the same wavelength, called elastic or Rayleigh scattering. A small amount (<0.001%) is scattered at different wavelengths, called inelastic or Raman scattering. Raman scatter is associated with rotational, vibrational, and electronic level transitions. Raman spectroscopy can reveal the chemical and structural composition of samples.

As used herein, "ultrafiltration" refers to a membrane process that is widely used for protein concentration in the downstream processing of protein therapeutics during the purification of recombinant proteins Ultrafiltration is a size-based separation, where species larger than the membrane pores are retained and smaller species pass through freely. During processing, the protein solution is pumped tangentially across the surface of a semi-permeable parallel flat sheet membrane. The membrane is permeable to buffer and buffer salts but generally impermeable to monoclonal antibodies. The driving force for permeation is applied transmembrane pressure (TMP) induced by flow restriction at the outlet of the membrane flow channel (TMP=$(P_{feed}+P_{retentate})/2-P_{permeate}$).

As used herein, "primary concentration" refers to the initial step where transmembrane pressure drives water and salts across the permeable membrane, which reduces the liquid volume and thus increases protein concentration. The extent of concentration in primary concentration may be optimized to balance throughput, protein stability, processing time and buffer consumption.

As used herein, "diafiltration" refers to a technique that uses a semi-permeable membrane to exchange a product of interest from one liquid medium into another. Buffer exchange and de-salting are typically performed using a diafiltration mode in which the small impurities and buffer components are effectively washed away from the product by the continuous addition of a buffer that is intended to condition the protein to a stable pH and excipient concentration that allows high product concentration. This can be performed in a continuous or discontinuous mode based on processing techniques.

Diafiltration is often combined with ultrafiltration to achieve the desired volume reduction while also removing impurities and salts. UF/DF is the final unit operation in downstream purification which conditions the mAb to achieve pH, excipient content, and protein concentration conducive to long term storage and addition of stabilizing excipients to generate Formulated Drug Substance (FDS).

As used herein, "final concentration" refers to the final step where transmembrane pressure drives water and salts across the permeable membrane, which reduces the liquid volume and thus increases protein concentration to the desired target for storage and/or formulation. The resultant pool from the final concentration step is final concentrated pool (FCP). This final concentration step can be performed in a continuous or discontinuous processing mode.

The terms "bioproduct" and "protein purification intermediate" can be used interchangeably and refer to any antibody, antibody fragment, modified antibody, protein, glycoprotein, or fusion protein as well as final drug substances purified from a bioreactor process.

The terms "control" and "controlling" refer to adjusting an amount or concentration level of a critical quality attribute in a harvested cell culture fluid to a predefined set point.

As used herein, the term "upstream processing" refers to the first step in which antibodies or therapeutic proteins are produced, usually by bacterial or mammalian cell lines, in bioreactors. Upstream processing includes media preparation, cell culture, and cell separation and harvest. When the cells have reached the desired density, they are harvested and moved to the downstream section of the bioprocess. The term "downstream processing" refers to the isolation and purification that occurs after the harvest of an antibody or therapeutic protein from a bioreactor. Typically, this means recovery of a product from an aqueous solution via several different modalities. The harvested product is processed to meet purity and critical quality attribute requirements during downstream processing.

As used herein, the term "protein purification intermediate" refers to a protein that has been harvested from a bioreactor and refers to any intermediate during downstream processing.

The term "concentrated protein purification intermediate" refers to a protein purification intermediate with a concentration greater than 5 mg/mL. More preferably the concentration is between 50 mg/mL to 300 mg/mL.

The terms "monitor" and "monitoring" refer to regularly checking an amount or concentration level of a critical quality attribute in a cell culture or a harvested cell culture fluid.

The term "harvested cell culture fluid" refers to fluid that is removed from a bioreactor containing cells that were engineered to secrete proteins of interest. The "harvested cell culture fluid" optimally contains the secreted protein of interest, for example a monoclonal antibody.

As used herein "critical quality attribute (CQA)" refers to a physical, chemical, biological, or microbiological property or characteristic that should be within an appropriate limit, range, or distribution to ensure the desired product quality of a biologic therapeutic drug product. These attributes have the potential to impact safety, efficacy, and/or potency. Critical quality attributes include but are not limited to protein concentration, high molecular weight species, buffer excipients, and pH.

As used herein, "formulated drug substance" refers to an active ingredient that is intended to furnish pharmacological activity, but does not include intermediates used in the synthesis of such ingredient.

As used herein, "universal model" refers to a mathematical correlation of spectral properties of different recombinant proteins used to predict a critical quality attribute.

As used herein, "mAb specific model" refers to a mathematical correlation of spectral properties of one particular protein used to predict a critical quality attribute.

As used herein "titer" refers to the amount of an antibody or protein molecules in a solution.

II. Systems and Methods for Characterization of Downstream Protein Purification Products Systems and methods for monitoring and controlling protein concentration during protein manufacturing are provided. Concentrated protein solutions are difficult to measure accurately due to high correlated solution viscosities (>10 cP). Accurate quantification requires specialty offline equipment and typically solution dilution. In high concentration UF/DF, final excipient levels are a function of protein concentration due to the Gibbs-Donnan effect. Real time monitoring and analysis during manufacturing is not available which increases processing time and potential batch failure due to not meeting CQAs. The systems and methods disclosed herein can be used for in-line monitoring of protein concentration and other critical quality attributes.

In one embodiment, the Raman spectroscopy system is an in-line or in situ Raman spectroscopy system used during production of a final concentrated pool, which could be highly concentrated (≥150 g/L). Typically, the Raman spectroscopy system is employed downstream of production of the protein purification intermediate, for example during processing of the protein purification intermediate after harvest from a bioreactor or fed-batch culture system and subsequent purification. FIG. 1 shows an exemplary protein purification process. Typically, the protein purification intermediate is harvested from cell culture (100) and processed through various purification steps such as affinity capture (110), viral inactivation (120), polishing chromatography (130 and 140), virus retentive filtration (150), and ultrafiltration/diafiltration (160), to produce the final concentrated pool which is then formulated to drug substance. In one embodiment, the monitoring of protein concentration in a harvested cell culture fluid is performed by in situ Raman spectroscopy.

A. Raman Spectroscopy

In one embodiment, monitoring and controlling protein concentration in a harvested cell culture fluid is performed by Raman spectroscopy. Raman spectroscopy is a form of vibrational spectroscopy that provides information about molecular vibrations that can be used for sample identification and critical quality attribute quantitation. In situ Raman analysis is a method of analyzing a sample in its original location without having to extract a portion of the sample for analysis in a Raman spectrometer. In situ Raman analysis is advantageous in that the Raman spectroscopy analyzers are noninvasive and nondestructive which reduces the risk of contamination and loss of protein quality. In-line Raman analysis can be implemented to enable continuous processing while monitoring protein concentration of harvested cell culture fluid, protein purification intermediates, and/or final concentrated pool.

The in situ Raman analysis can provide real-time assessments of protein concentration in protein purification intermediates. For example, the raw spectral data provided by in situ Raman spectroscopy can be used to obtain and monitor the current protein concentration in protein purification intermediates. In this aspect, to ensure that the raw spectral data is continuously up to date, the spectral data from the Raman spectroscopy should be acquired about every 5 seconds to 10 hours. In another embodiment, the spectral data should be acquired about every 15 minutes to 1 hour. In still another embodiment, the spectral data should be acquired about every 20 minutes to 30 minutes.

The monitoring of the protein concentration in the protein purification intermediate can be analyzed by any commercially available Raman spectroscopy analyzer that allows for in situ Raman analysis. The in situ Raman analyzer should be capable of obtaining raw spectral data within the protein purification intermediate. For example, the Raman analyzer should be equipped with a probe that may be inserted inline of the fluid circuit. Suitable Raman analyzers include, but are not limited to, RamanRXN2 and RamanRXN4 analyzers (Kaiser Optical Systems, Inc. Ann Arbor, Mich.).

The raw spectral data obtained by in situ Raman spectroscopy may be compared to offline protein concentration measurements in order to correlate the peaks within the spectral data to the protein concentration. Offline protein concentration measurements may be used to determine which spectral regions exhibit the protein signal. The offline measurement data may be collected through any appropriate analytical method. In the case of protein concentration, for example, the offline measurement can be collected using SoloVPE (C-technologies). Additionally, any type of multivariate software package, for example, SIMCA 13 (MKS Data Analytic Solutions, Umea, Sweden), may be used to correlate the peaks within the raw spectral data to offline measurements of protein concentration. However, in some embodiments, it may be necessary to pretreat the raw spectral data with spectral filters to remove any varying baselines. For example, the raw spectral data may be pretreated with any type of point smoothing technique or normalization technique. Normalization may be needed to correct for any probe, optic, laser power variation and exposure time by the Raman analyzer. In one embodiment, the raw spectral data may be treated with point smoothing, such as 1st derivative with 21 $cm^{-1}$ point smoothing, and normalization, such as Standard Normal Variate (SNV) normalization. These pre-processing techniques may be combined for certain spectral regions to improve the model predictions.

Chemometric modeling may also be performed on the obtained spectral data. In this aspect, one or more multivariate methods including, but not limited to, Partial Least Squares (PLS), Principal Component Analysis (PCA), Orthogonal Partial least squares (OPLS), Multivariate Regression, Canonical Correlation, Factor Analysis, Cluster Analysis, Graphical Procedures, and the like, can be used on the spectral data. In one embodiment, the obtained spectral data is used to create a PLS regression model. A PLS regression model may be created by projecting predicted variables and observed variables to a new space. In this aspect, a PLS regression model may be created using the measurement values obtained from the Raman analysis and the offline measurement values. The PLS regression model provides predicted process values, for example, predicted protein concentration value. In one embodiment, the model provides predicted protein concentration values with ≤5% error compared to off-line protein concentration values. In a preferred embodiment, the model provides predicted protein concentration values with ≤3% error compared to off-line protein concentration values.

After chemometric modeling, a signal processing technique may be applied to the predicted protein concentration values. In one embodiment, the signal processing technique will dampen model variability and prediction error. In this aspect, one or more of the pre-processing techniques may be applied to the predicted protein concentration values. Any pre-processing techniques known to those skilled in the art may be utilized. For example, the noise reduction technique may include data smoothing and/or signal rejection. Smoothing is achieved through a series of smoothing algorithms and filters while signal rejection uses signal characteristics to identify data that should not be included in the analyzed spectral data. In one embodiment, the predicted protein concentration values are noise mitigated by a noise reduction filter. The noise reduction filter provides final predicted protein concentration values. In this aspect, the noise reduction technique combines raw measurements with a model-based estimate for what the measurement should yield according to the model. In one embodiment, the noise reduction technique combines a current predicted protein concentration value with its uncertainties. Uncertainties can be determined by the repeatability of the predicted protein concentration values and the current protein concentration values. Once the next predicted protein concentration value is observed, the estimate of the predicted protein concentration value is updated using a weighted average where more weight is given to the estimates with higher certainty. Using an iterative approach, the final protein concentration values may be updated based on the previous measurement and the current measurement. In this aspect, the algorithm should be recursive and able to run in real time so as to utilize the current predicted protein concentration value, the previous value, and experimentally determined constants. The noise reduction technique improves the robustness of the measurements received from the Raman analysis and the PLS predictions by reducing noise upon which the automated feedback controller will act.

B. Methods of Use

The disclosed methods can be used to monitor and control protein concentration in harvested cell culture and/or protein purification intermediates fluids during downstream protein purification processes. Common downstream purification processes include but are not limited to centrifugation, direct depth filtration, protein A affinity purification, viral inactivation steps, ion-exchange chromatography, hydrophobic interaction chromatography, size-exclusion chromatography, ultrafiltration/diafiltration, viral retentive filtration, and combinations thereof. These unit operations are used in a defined sequential combination to isolate the protein of interest and ensure impurities and/or critical quality attributes are monitored prior to the production of formulated drug substance. In one embodiment, the disclosed methods include a Raman probe in-line of the fluid circuit. In another embodiment, the disclosed methods can be used to produce a concentrated protein purification intermediate or final concentrated pool.

1. Antibody Titer and Protein Concentration

Both antibody titer and protein concentration are important factors in the purification of bioproducts. Antibody titer measured after the initial harvest of the cell culture fluid is important to determine column loadings and ensure a robust purification process for removal of impurities. Monitoring protein concentration throughout purification steps is important to ensure both the proper concentration of end product, and proper performance of the purification unit operations performed. Improper protein concentration can lead to ineffective drug products or production of formulated drug substance.

In one embodiment, harvested cell culture fluid is subjected to Raman spectral analysis immediately after being harvested, but before any additional purification has begun. Raman spectral data can be used after harvest to quantify antibody titer in the harvested cell culture fluid. Protein concentration can be measured using the disclosed methods at multiple steps during the protein purification process, for example, during affinity capture, during polishing chromatography, during virus retentive filtration, or during ultrafiltration/diafiltration. Inline Raman probes can detect Raman scattering in the harvested cell culture fluid and/or protein purification intermediate within the fluid circuit without removing sample from the system providing analytical characterizations that are normally determined in an offline fashion.

In one embodiment, if the protein concentration is not within the pre-determined concentration during ultrafiltration/diafiltration, the system is notified and the protein purification intermediate is altered accordingly. For example, if the protein concentration in the protein purification intermediate is below the predetermined protein concentration the protein purification intermediate can be further concentrated by performing ultrafiltration/diafiltration.

In one embodiment, the concentration step is performed by Protein A affinity chromatography.

2. Drug-to-Antibody Ratio

In another embodiment, the disclosed methods can be used to monitor and control drug-to-antibody ratio (DAR). DAR is a quality attribute that is monitored during development of antibody-drug conjugates (ADC), antibody-radionuclide conjugates (ARC), and general protein conjugates (potent steroids, non-cytotoxic payloads, etc.) to ensure consistent product quality and to facilitate subsequent labeling with payloads. DAR is the average number of drugs or other therapeutic molecules conjugated to antibodies, and is an important quality attribute in the production of therapeutic conjugates. The DAR value affects the efficacy of the conjugated drug as low drug loading reduces the drug potency while high loading can negatively affect the pharmacokinetics and safety.

In one embodiment, antibody-radionuclide conjugates are subjected to Raman spectral analysis immediately after being conjugated, but before any additional purification occurs. Raman spectral data can be used after conjugation to determine the DAR.

In one embodiment, if the DAR is not within the pre-determined concentration during processing, the system is notified and the ADC intermediate is altered accordingly. For example, if the DAR in the ADC intermediate is below the predetermined DAR the conjugation reaction components can be altered, for example reactant concentrations can be optimized, the type of linker can be altered, temperature, or other manufacturing variables can be optimized.

3. Buffer Excipients

The disclosed methods can be used to monitor and control the levels of buffer excipients in harvested cell culture fluid and/or protein purification intermediate during downstream purification. Buffer excipients that are commonly used in monoclonal antibody productions include but are not limited to acetate, citrate, histidine, succinate, phosphate, and hydroxymethylaminomethane (Tris), proline, and arginine. Surfactant excipients include but are not limited to polysorbate 80 (Tween 80), polysorbate 20 (Tween 20), and poloxamer 188. Polyol/disaccharide/polysaccharide excipients include but are not limited to mannitol, sorbitol, sucrose, and dextran 40. Antioxidant excipients include but are not limited to ascorbic acid, methionine, and ethylenediaminetetraacetic acid (EDTA). Two commonly used amino acid excipients are histidine and arginine. In a preferred embodiment, the excipient that is monitored and controlled is histidine and arginine.

Final concentrated pool excipient concentrations differ from the composition of the diafiltration buffer due to the combination of the excluded volume and Donnan effects. The Donnan effect is a phenomenon that arises due to retention of the net positively charged protein by the membrane during UF/DF combined with the requirement for charge neutrality in both the retentate and permeates. To balance the positively charged protein, negatively charged buffer components are enriched in the retentate relative to the diafiltration buffer, while positively charged buffer components are expelled. This effect can lead to FCP pH and buffer excipient concentrations differing substantially from the diafiltration buffer composition (Stoner, et al., *J Pharm Sci*, 93:2332-2342 (2004)).

Volume exclusion describes the behavior of highly concentrated samples in which protein occupies a significant fraction of the solution volume. Buffer is excluded from the volume occupied by the protein, causing the buffer solute concentrations to decrease as protein concentration increases expressed as moles (or mass) of solute per solution volume. Buffer is excluded from the volume occupied by the protein, causing the buffer solute concentrations to decrease as protein concentration increases when expressed as moles (or mass) of solute per solution volume.

Based on both of these principles and buffer excipient levels being critical quality attributes, inline Raman probes will minimize offline analytical characterization and provide further process understanding to ensure excipient levels are sufficient prior to formulation.

4. High Molecular Weight Impurities

In production of monoclonal antibodies, low levels of products-related impurities often exist even after extensive purification steps. High molecular weight (HMW) species (e.g., antibody dimer species) are a product-related impurity that contributes to size heterogeneity of mAb products. The formation of HMW species within a therapeutic mAb drug product as a result of protein aggregation can potentially compromise both drug efficacy and safety. HMW species are considered a CQA that are routinely monitored during drug development and as part of release testing of purified protein drug products during manufacturing.

In one embodiment, the disclosed methods can be used to identify protein drug products that contain HMW species. HMW species can be detected by Raman spectroscopy at various steps during the purification process including but not limited to during affinity capture, during viral inactivation, during polishing chromatography, during virus retentive filtration, during ultrafiltration/diafiltration, or combinations thereof.

In one embodiment, the disclosed methods detect HMW species in the harvested cell culture fluid and the fluid is further processed to remove the HMW species. Methods of removing HMW species for cell culture fluid include additional polishing steps including but not limited to cation exchange chromatography and anion exchange chromatography.

C. UF/DF Systems

Figure 6:
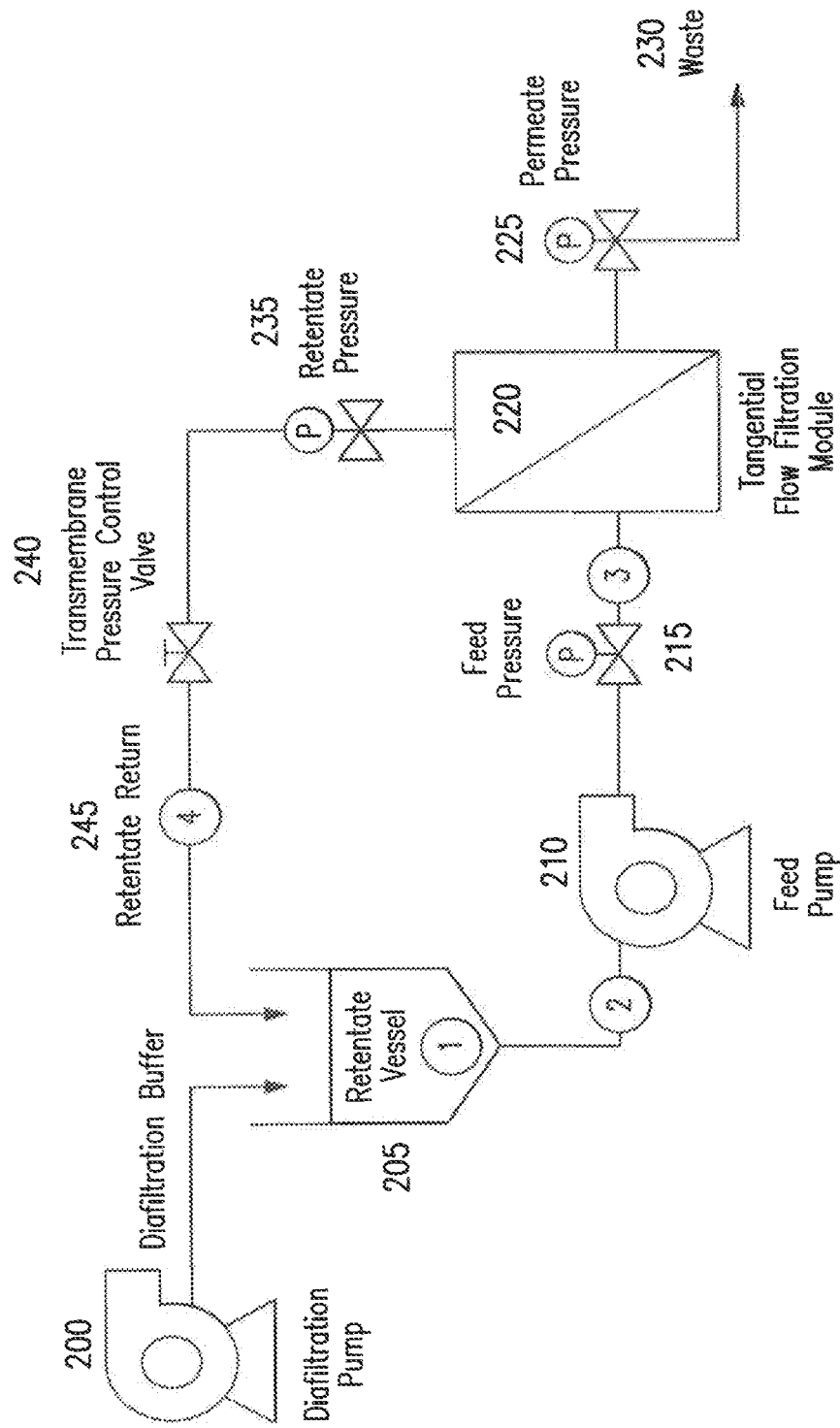
FIG. 6 is a schematic illustration of an ultrafiltration/diafiltration system, including locations for inline Raman probe placement.

FIG. 6 illustrates an ultrafiltration/diafiltration processing system, including various locations for in-line Raman probes (circled numbers 1-4). Protein purification intermediate is pumped into a retentate vessel 205 by a diafiltration pump 200 which may be a peristaltic, rotary lobe, pressure transfer, or diaphragm pump. Fluid from retentate vessel 205 flows to feed pump 210 which may be either a rotary lobe, peristaltic or diaphragm pump, past feed pressure valve 215 and into tangential flow filtration module (TFFM) 220. In TFFM 220 the protein purification intermediate is subjected to ultrafiltration across a membrane. The bioproduct of interest is retained in the fluid (retentate) while water and low molecular weight solutes including buffer excipients pass through the membrane in the permeate (filtrate) which exits the system by passing through permeate pressure valve 225 into waste tank 230. The retentate exits TFFM 220 and passes through retentate pressure valve 235, transmembrane pressure control valve 240, and retentate return channel 245 wherein it flows back into retentate vessel 205. The process can be repeated as necessary to concentrate the bioproduct, remove impurities, and ensure CQAs are within acceptable limits. During diafiltration the same flow path described above is followed where permeable solutes are replaced as new buffer is washed into the product stream. When new buffer is added at the same rate as permeate is removed from the system, the sum of the retentate tank and skid hold-up volume defines the system volume. One turn-over volume (TOV) is defined as an amount of diafiltration buffer added to the UF/DF process equal to the system volume. Typically, replacement of 8-times system volume (8 TOV) assures >99.9% buffer exchange (Schwarts, L., *Scientific and Technical Report*, PN 33289)

Additionally, during the UF/DF process, it is necessary to mix the protein solution in the retentate vessel 205. Differences in density between the diafiltration buffer, the retentate return, and bulk retentate during diafiltration require that agitation in the tank should be sufficient to ensure adequate buffer exchange, yet sufficiently moderate to avoid sheer, as this has been observed to result in protein aggregation and subvisible particle (SVP) generation in certain products. Additionally, it is important to ensure adequate mixing of retentate return during concentration stages to prevent protein concentration polarization in the retentate tank resulting in higher protein concentrations being delivered to the UF/DF membranes.

In one embodiment the Raman probe is placed at location 1, downstream of diafiltration pump 200 in retentate vessel 205. The Raman probe could alternatively be placed at location 2 downstream of retentate vessel 205 inline before feed pump 210. In another embodiment, the Raman probe is placed inline at location 3 between feed pressure pump 215 and tangential flow filtration module 220. In yet another embodiment, the Raman probe is placed inline in retentate return 245. The location of the Raman probe is critical to ensure accurate inline measurements in a complicated system that has engineering and processing constraints.

D. Cell Culture

The harvested cell culture fluid can be harvested from a bioreactor containing cells engineered to produce monoclonal antibodies. The term "cell" includes any cell that is suitable for expressing a recombinant nucleic acid sequence. Cells include those of prokaryotes and eukaryotes, such as bacterial cells, mammalian cells, human cells, non-human animal cells, avian cells, insect cells, yeast cells, or cell fusions such as, for example, hybridomas or quadromas. In certain embodiments, the cell is a human, monkey, ape, hamster, rat or mouse cell. In other embodiments, the cell is selected from the following cells: Chinese Hamster Ovary (CHO) (e.g. CHO K1, DXB-11 CHO, Veggie-CHO), COS (e.g. COS-7), retinal cell, Vero, CV1, kidney (e.g. HEK293, 293 EBNA, MSR 293, MDCK, HaK, BHK21), HeLa, HepG2, W138, MRC 5, Colo25, HB 8065, HL-60, lymphocyte, e.g. Jurkat (T lymphocyte) or Daudi (B lymphocyte), A431 (epidermal), U937, 3T3, L cell, C127 cell, SP2/0, NS-0, MMT cell, stem cell, tumor cell, and a cell line derived from an aforementioned cell. In some embodiments, the cell comprises one or more viral genes, e.g. a retinal cell that expresses a viral gene (e.g. a PER.C6® cell). In some embodiments, the cell is a CHO cell. In other embodiments, the cell is a CHO K1 cell.

In protein production, a "fed-batch cell culture" or "fed-batch culture" refers to a batch culture wherein the cells and culture medium are supplied to the culturing vessel initially, and additional culture nutrients are slowly fed, in discrete increments, to the culture during culturing, with or without periodic cell and/or product harvest before termination of culture. Fed-batch culture includes "semi-continuous fed-batch culture" wherein periodically whole culture (which may include cells and medium) is removed and replaced by fresh medium. Fed-batch culture is distinguished from simple "batch culture" whereas all components for cell culturing (including the animal cells and all culture nutrients) are supplied to the culturing vessel at the start of the culturing process in batch culture. Fed-batch culture may be different from "perfusion culture" insofar as the supernatant is not removed from the culturing vessel during a standard fed-batch process, whereas in perfusion culturing, the cells are restrained in the culture by, e.g., filtration, and the culture medium is continuously or intermittently introduced and removed from the culturing vessel. However, removal of samples for testing purposes during fed-batch cell culture is contemplated. The fed-batch process continues until it is determined that maximum working volume and/or protein production is reached, and protein is subsequently harvested.

The phrase "continuous cell culture" relates to a technique used to grow cells continually, usually in a particular growth phase. For example, if a constant supply of cells is required, or the production of a particular protein of interest is required, the cell culture may require maintenance in a particular phase of growth. Thus, the conditions must be continually monitored and adjusted accordingly in order to maintain the cells in that particular phase.

The terms "cell culture medium" and "culture medium" refer to a nutrient solution used for growing mammalian cells that typically provides the necessary nutrients to enhance growth of the cells, such as a carbohydrate energy source, essential (e.g. phenylalanine, valine, threonine, tryptophan, methionine, leucine, isoleucine, lysine, and histidine) and nonessential (e.g. alanine, asparagine, aspartic acid, cysteine, glutamic acid, glutamine, glycine, proline, serine, and tyrosine) amino acids, trace elements, energy sources, lipids, vitamins, etc. Cell culture medium may contain extracts, e.g. serum or peptones (hydrolysates), which supply raw materials that support cell growth. Media may contain yeast-derived or soy extracts, instead of animal-derived extracts. Chemically defined medium refers to a cell culture medium in which all of the chemical components are known (i.e. have a known chemical structure). Chemically defined medium is entirely free of animal-derived components, such as serum- or animal-derived peptones. In one embodiment, the medium is a chemically defined medium.

The solution may also contain components that enhance growth and/or survival above the minimal rate, including hormones and growth factors. The solution may be formulated to a pH and salt concentration optimal for survival and proliferation of the particular cell being cultured.

E. Proteins of Interest

Any protein of interest suitable for expression in prokaryotic or eukaryotic cells can be monitored using the disclosed methods. For example, the protein of interest includes, but is not limited to, an antibody or antigen-binding fragment thereof, a chimeric antibody or antigen-binding fragment thereof, an ScFv or fragment thereof, an Fc-fusion protein or fragment thereof, a growth factor or a fragment thereof, a cytokine or a fragment thereof, or an extracellular domain of a cell surface receptor or a fragment thereof. Proteins of interest may be simple polypeptides consisting of a single subunit, or complex multisubunit proteins comprising two or more subunits. The protein of interest may be a biopharmaceutical product, food additive or preservative, or any protein product subject to purification and quality standards.

In some embodiments, the antibody is selected from the group consisting of an anti-Programmed Cell Death 1 antibody (e.g., an anti-PD1 antibody as described in U.S. Pat. No. 9,987,500), an anti-Programmed Cell Death Ligand-1 (e.g., an anti-PD-L1 antibody as described in U.S. Pat. No. 9,938,345), an anti-D114 antibody, an anti-Angiopoetin-2 antibody (e.g., an anti-ANG2 antibody as described in U.S. Pat. No. 9,402,898), an anti-Angiopoetin-Like 3 antibody (e.g., an anti-AngPtl3 antibody as described in U.S. Pat. No. 9,018,356), an anti-platelet derived growth factor receptor antibody (e.g., an anti-PDGFR antibody as described in U.S. Pat. No. 9,265,827), an anti-Erb3 antibody, an anti-Prolactin Receptor antibody (e.g., anti-PRLR antibody as described in U.S. Pat. No. 9,302,015), an anti-Complement 5 antibody (e.g., an anti-C5 antibody as described in U.S. Pat. No. 9,795,121), an anti-TNF antibody, an anti-epidermal growth factor receptor antibody (e.g., an anti-EGFR antibody as described in U.S. Pat. No. 9,132,192 or an anti-EGFRvIII antibody as described in U.S. Pat. No. 9,475,875), an anti-Proprotein Convertase Subtilisin Kexin-9 antibody (e.g., an anti-PCSK9 antibody as described in U.S. Pat. Nos. 8,062,640 or 9,540,449), an anti-Growth And Differentiation Factor-8 antibody (e.g. an anti-GDF8 antibody, also known as anti-myostatin antibody, as described in U.S. Pat. Nos. 8,871,209 or 9,260,515), an anti-Glucagon Receptor (e.g., anti-GCGR antibody as described in U.S. Pat. Nos. 9,587,029 or 9,657,099), an anti-VEGF antibody, an anti-IL1R antibody, an interleukin 4 receptor antibody (e.g., an anti-IL4R antibody as described in U.S. Pat. Appln. Pub. No. US2014/0271681A1 or U.S. Pat. Nos. 8,735,095 or 8,945,559), an anti-interleukin 6 receptor antibody (e.g., an anti-IL6R antibody as described in U.S. Pat. Nos. 7,582,298, 8,043,617 or 9,173,880), an anti-IL1 antibody, an anti-IL2 antibody, an anti-IL3 antibody, an anti-IL4 antibody, an anti-IL5 antibody, an anti-1L6 antibody, an anti-1L7 antibody, an anti-interleukin 33 (e.g., anti-IL33 antibody as described in U.S. Pat. Nos. 9,453,072 or 9,637,535), an anti-Respiratory syncytial virus antibody (e.g., anti-RSV antibody as described in U.S. Pat. No. 9,447,173), an anti-Cluster of differentiation 3 (e.g., an anti-CD3 antibody, as described in U.S. Pat. Nos. 9,447,173 and 9,447,173, and in U.S. Application No. 62/222,605), an anti-Cluster of differentiation 20 (e.g., an anti-CD20 antibody as described in U.S. Pat. No. 9,657,102 and US20150266966A1, and in U.S. Pat. No. 7,879,984), an anti-CD19 antibody, an anti-CD28 antibody, an anti-Cluster of Differentiation-48 (e.g. anti-CD48 antibody as described in U.S. Pat. No. 9,228,014), an anti-Fel d1 antibody (e.g. as described in U.S. Pat. No. 9,079,948), an anti-Middle East Respiratory Syndrome virus (e.g. an anti-MERS antibody as described in U.S. Pat. No. 9,718,872), an anti-Ebola virus antibody (e.g., as described in U.S. Pat. No. 9,771,414), an anti-Zika virus antibody, an anti-Lymphocyte Activation Gene 3 antibody (e.g., an anti-LAG3 antibody, or an anti-CD223 antibody), an anti-Nerve Growth Factor antibody (e.g., an anti-NGF antibody as described in U.S. Pat. Appln. Pub. No. US2016/0017029 and U.S. Pat. Nos. 8,309,088 and 9,353,176) and an anti-Activin A antibody.

In some embodiments, the bispecific antibody is selected from the group consisting of an anti-CD3×anti-CD20 bispecific antibody (as described in U.S. Pat. No. 9,657,102 and U.S. Pat. Appln. Pub. No. US20150266966A1), an anti-CD3×anti-Mucin 16 bispecific antibody (e.g., an anti-CD3×anti-Muc16 bispecific antibody), and an anti-CD3×anti-Prostate-specific membrane antigen bispecific antibody (e.g., an anti-CD3×anti-PSMA bispecific antibody). In some embodiments, the protein of interest is selected from the group consisting of abciximab, adalimumab, adalimumab-atto, ado-trastuzumab, alemtuzumab, alirocumab, atezolizumab, avelumab, basiliximab, belimumab, benralizumab, bevacizumab, bezlotoxumab, blinatumomab, brentuximab vedotin, brodalumab, canakinumab, capromab pendetide, certolizumab pegol, cemiplimab, cetuximab, denosumab, dinutuximab, dupilumab, durvalumab, eculizumab, elotuzumab, emicizumab-kxwh, emtansinealirocumab, evinacumab, evolocumab, fasinumab, golimumab, guselkumab, ibritumomab tiuxetan, idarucizumab, infliximab, infliximab-abda, infliximab-dyyb, ipilimumab, ixekizumab, mepolizumab, necitumumab, nesvacumab, nivolumab, obiltoxaximab, obinutuzumab, ocrelizumab, ofatumumab, olaratumab, omalizumab, panitumumab, pembrolizumab, pertuzumab, ramucirumab, ranibizumab, raxibacumab, reslizumab, rinucumab, rituximab, sarilumab, secukinumab, siltuximab, tocilizumab, tocilizumab, trastuzumab, trevogrumab, ustekinumab, and vedolizumab.

EXAMPLES

Example 1: Universal in-Line Protein Concentration Model for UF/DF Applications Materials and Methods The data collection for the model included spectral data from Raman Rxn2 and Rxn 4 analyzers (Kaiser Optical Systems, Inc. Ann Arbor, Mich.) utilizing MR-Probe-785 and RamanRxn Probehead-758 (Kaiser Optical Systems, Inc. Ann Arbor, Mich.). Additionally, several different optics were used throughout development based on availability. Raman analyzers operating parameters were set to a 10 second scan time for 6 accumulations, repeated 5 times. SIMCA 13 (MKS Data Analytic Solutions, Umea, Sweden) was used to correlate peaks within the spectral data to offline protein concentration measurements. Inline measurements were made throughout different points of UF/DF unit operation including primary concentration, diafiltration, and final concentration. Offline protein concentrations were determined using SoloVPE (C Technologies, Inc.). SoloVPE measurements were made in triplicate.

Figure 2:
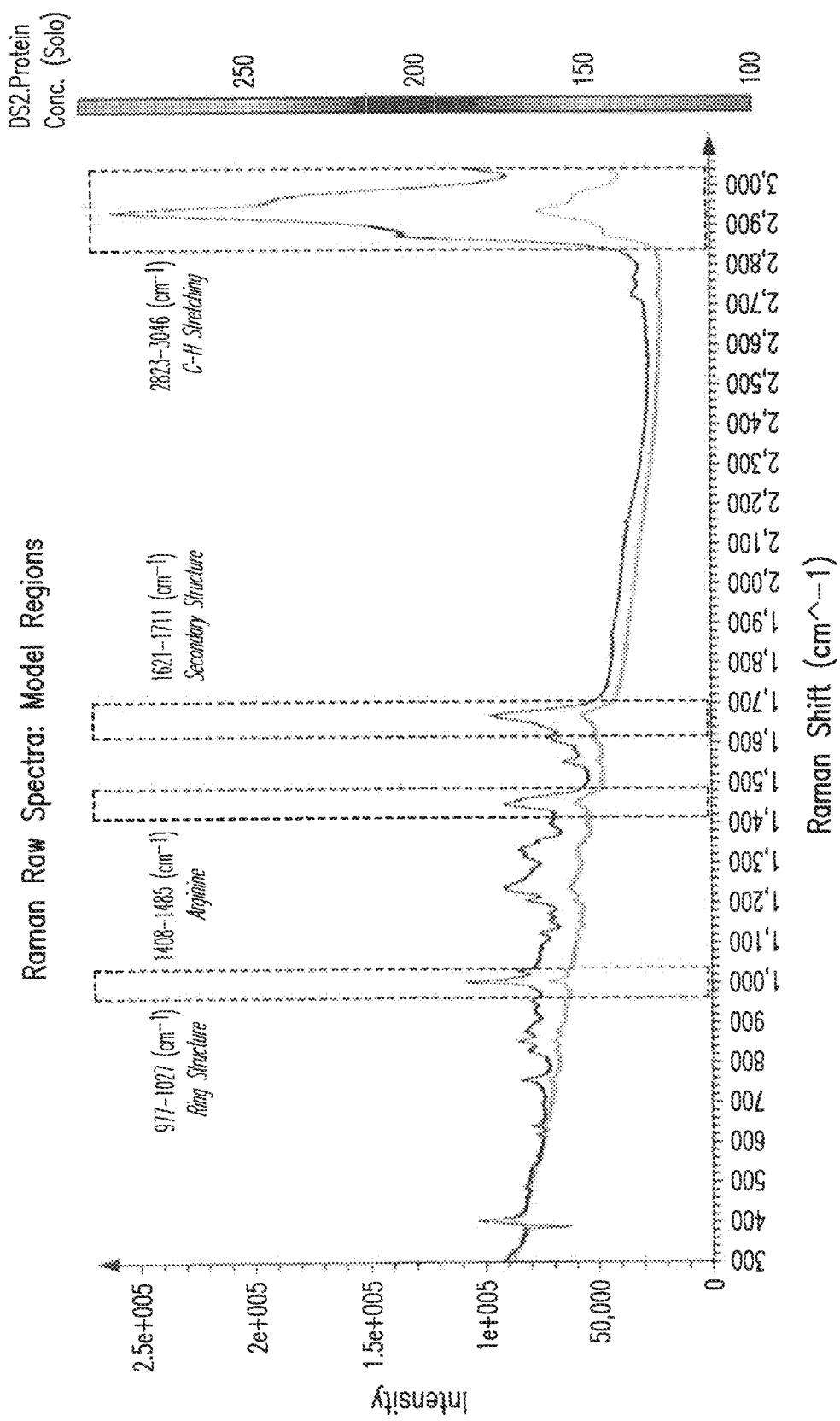
FIG. 2 is a representative spectrograph showing the initial model development for in-line Raman spectroscopy. The X axis represents the Raman shift. The Y axis represents intensity. The legend on the right represents protein concentration. Spectral regions used during the initial model development include, from left to right, 977-1027 $cm^{-1}$ (Ring structure), 1408-1485 $cm^{-1}$ (Arginine), 1621-1711 $cm^{-1}$ (Secondary structure), and 2823-3046 $cm^{-1}$ (C—H stretching).
Figure 3:
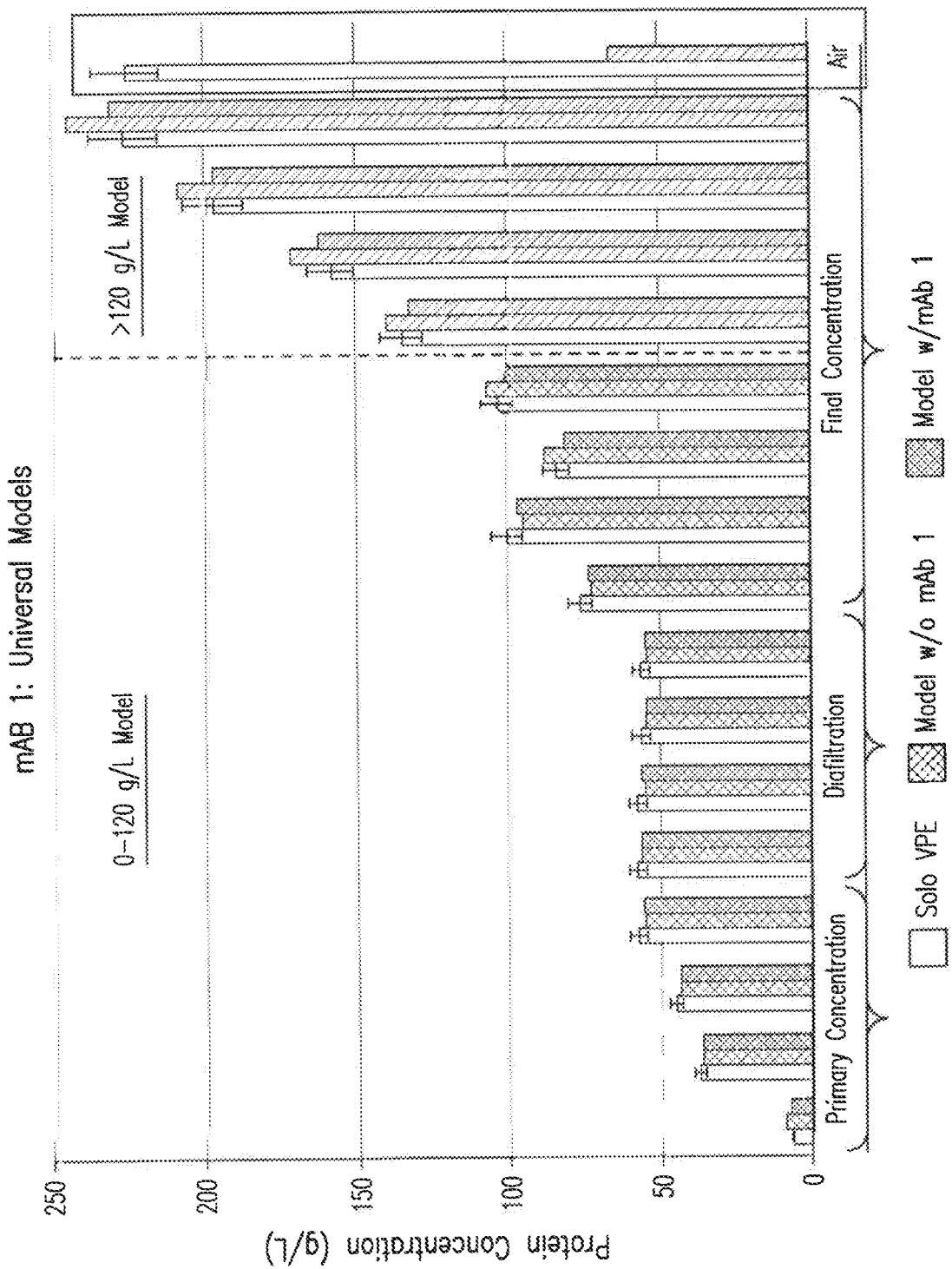
FIG. 3 is a bar graph showing protein concentration (g/L) for mAb1 during a standard ultrafiltration/diafiltration unit operation. The empty bars are concentrations determined using the UV-Vis based offline method with a SoloVPE system (C-technologies) with error bars of ±5% which is the goal for the inline Raman predictions. The bars with wide hatching represent the model herein referred to as the universal model without mAb1 included in the Raman predictions and the bars with narrow hatching represent the universal model with mAb1. The cross-hatched bars correspond to the predictions from the initial universal model with a range of 0-120 g/L. The hatched bars correspond to the predictions from the initial universal model >120 g/L.

FIG. 2 shows the spectral regions that were used for making the chemometric models. The regions included region 1-977-1027 $cm^{-1}$ (Ring structure), region 2-1408-1485 $cm^{-1}$ (Arginine), region 3-1621-1711 $cm^{-1}$ (Secondary structure), and region 4-2823-3046 $cm^{-1}$ (C—H stretching). The following spectral filtering was performed on the raw spectral data: 1st derivative with 21 $cm^{-1}$ point smoothing to remove varying baselines Results To determine the feasibility of a universal inline protein concentration model for ultrafiltration/diafiltration (UF/DF) applications mAb1 was analyzed using Raman spectroscopy. Protein concentration was measured before diafiltration (primary concentration), during diafiltration (diafiltration), and after diafiltration (final concentration). The calculated concentrations from the model were compared to the protein concentration determined by SoloVPE (FIG. 3). The model error for 0-120 g/L (primary concentration and diafiltration) was 3.1% and the model error for >120 g/L (final concentration) was 1.8% when the training set data was included (mAb 1 spectra incorporated into PLS model).

Processing errors can be detected by Raman spectroscopy. FIG. 3 shows that air entrainment in the system during final recirculation through the UF/DF system was detected by the Raman spectral data. The bars bounded by the rectangle show that the predicted concentration of mAb1 by SoloVPE was >200 g/L while the Raman prediction was ~65 g/L.

Figure 4:
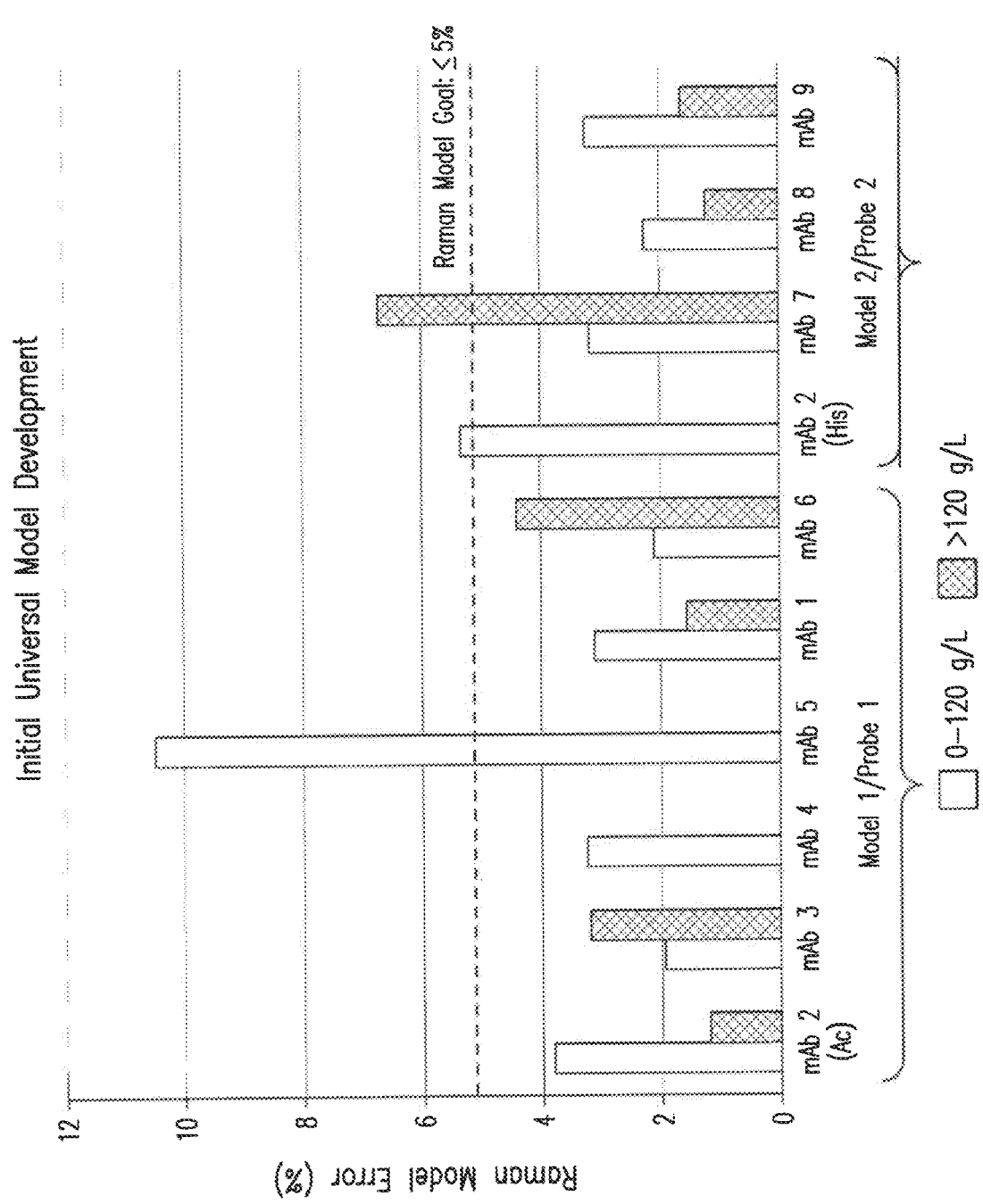
FIG. 4 is a bar graph showing absolute Raman model error for various mAbs from the initial universal model development. The hatched bars represent the initial universal model 0-120 g/L (Primary concentration and Diafiltration) and the empty bars represent from the initial universal model >120 g/L. (Final Concentration). The horizontal line represents the ≤5% error Raman model goal.

FIG. 4 shows absolute Raman model error for ten representative mAbs. This data showed the successful development of models for the mAbs shown which included different mAb isotypes (IgG1 and IgG4) as well as bispecific molecules. 14 out of 17 model predictions met ≤5% error. However, specific models (0-120 g/L and >120 g/L) were created for each probe that was used during development as probe to probe variability inflated the errors predicted by the PLS models.

Figure 5:
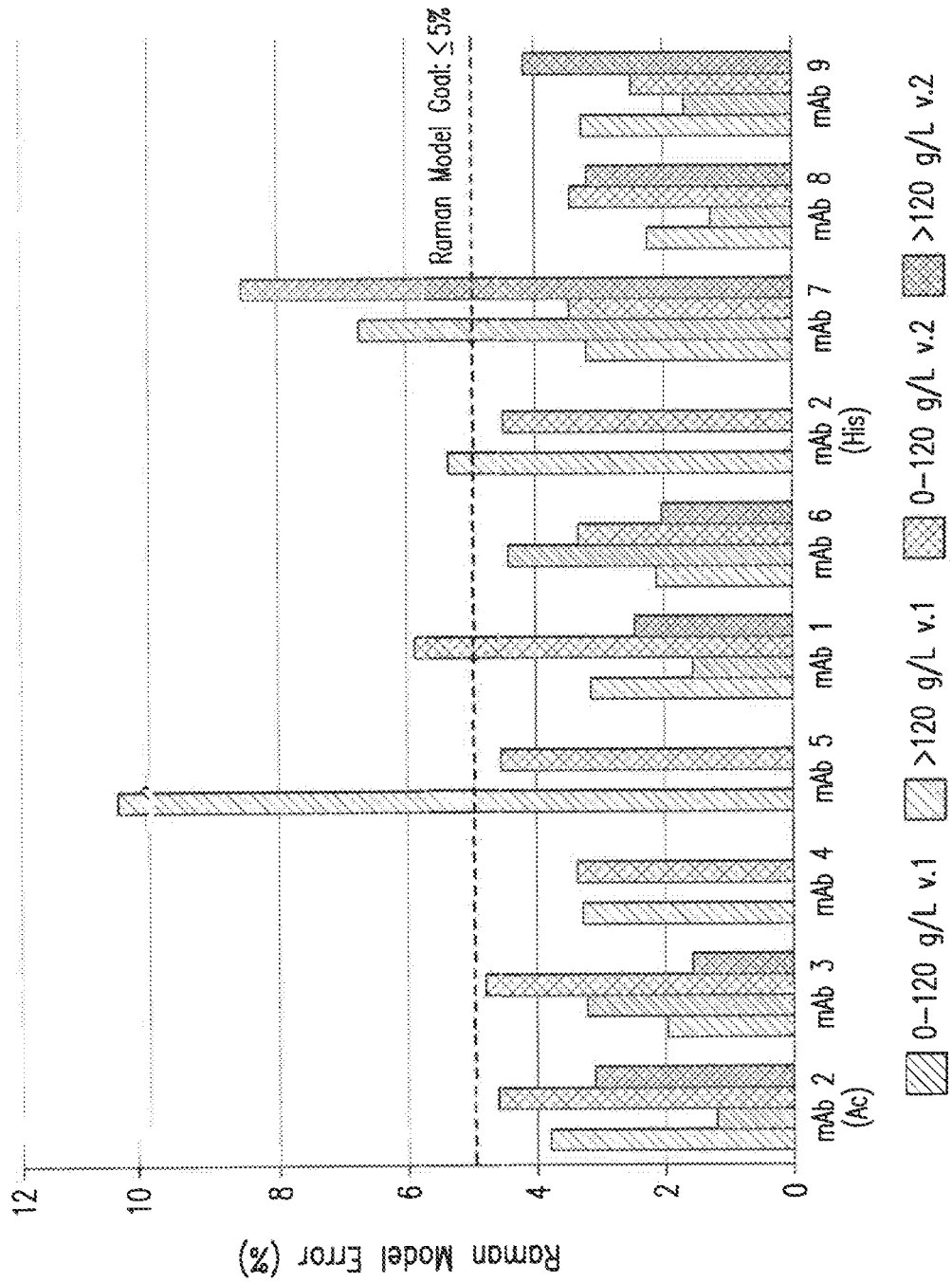
FIG. 5 is a bar graph showing absolute Raman model error for various mAbs. The bars with wide hatching represent 0-120 g/L (Primary concentration and diafiltration) and the bars with narrow hatching represent >120 g/L (final concentration). The horizontal line represents the ≤5% error Raman model goal. Two versions of the universal Raman model are shown. The hatched bars represent the initial universal model and the cross-hatched bars represent the updated universal model.

To optimize the model, different probes and lasers were tested in line with multiple mAbs. Model refinement was performed where only one spectral region was the focus of the updated universal model: 2823-3046 $cm^{-1}$ (C—H stretching) with a spectral filtering of Standard Normal Variant (SNV) to correct for laser power variation and probe variability as a baseline correction. A comparison of the two model components developed is summarized in Table 1. Partial Least Squares (PLS) regression models were created with corresponding offline SoloVPE measurements performed in triplicate. The Partial Least Squares Regression Model details are shown in Table 2. The updated dataset predicted with an optimized laser/probe universal model showed 15 out of 17 model predictions meeting ≤5% error compared to previous 14 out of 17 (FIG. 5).

TABLE 1

Universal Model Components Comparison

| Component Description | Universal Model (v. 1) | Universal Model (v. 2) |
|---|---|---|
| Laser | 1 | 3 |
| Optics | 2 | 6 |
| Preprocessing filter | 1st Derivative with 21 $cm^{-1}$ point smoothing | Standard Normal Variant (SNV) |
| Spectral Regions | 977-1027 $cm^{-1}$ 1408-1485 $cm^{-1}$ 1621-1711 $cm^{-1}$ 2823-3046 $cm^{-1}$ | 2823-3046 $cm^{-1}$ |

TABLE 2

Protein Concentration Partial Least Squares Regression Universal Model (v. 2) Details

| Final Models | 0-120 g/L | >120 g/L |
|---|---|---|
| Sample Size | 1412 | 879 |
| $R^2X$ | 0.993 | 0.987 |
| $Q^2$ | 0.984 | 0.958 |
| RMSECV | 3.34 | 7.77 |

$R^2X$—Percent of variation explained by the model, Target: $R^2 > 0.9$
$Q^2$—Percent of variation predicted by the model during cross-validation, Target: $Q^2 > 0.8$
RMSECV: Root mean square error of cross-validation

Example 2: Scale-Up Performance of Protein Concentration Models

Materials and Methods

The optimized Universal models (v.2) (see Table 1) were tested with a scale-up ½" Single Use Tangential Flow Filtration System (Pall Corporation) experiment with mAb10. The mAb10 load material was formulated drug substance, rather than typical processing load material. The FDS material was diluted to representative UF/DF load source including protein concentration and buffer excipients. However, due to the presence of additional excipients in load source that had not been tested during the universal model development, mAb 10 specific models were created. Refer to example 1 for methods for Raman data collection and scan length information. The mAb specific model for >120 g/L used the same spectral regions and pre-processing techniques as the Universal model (v. 2). However, the 0-120 g/L mAb specific model used the four spectral regions as shown in FIG. 2 with Standard Normal Variant pre-processing. The differences in the 0-120 g/L model can be attributed to the additional excipients in the load source.

Results

Figure 7:
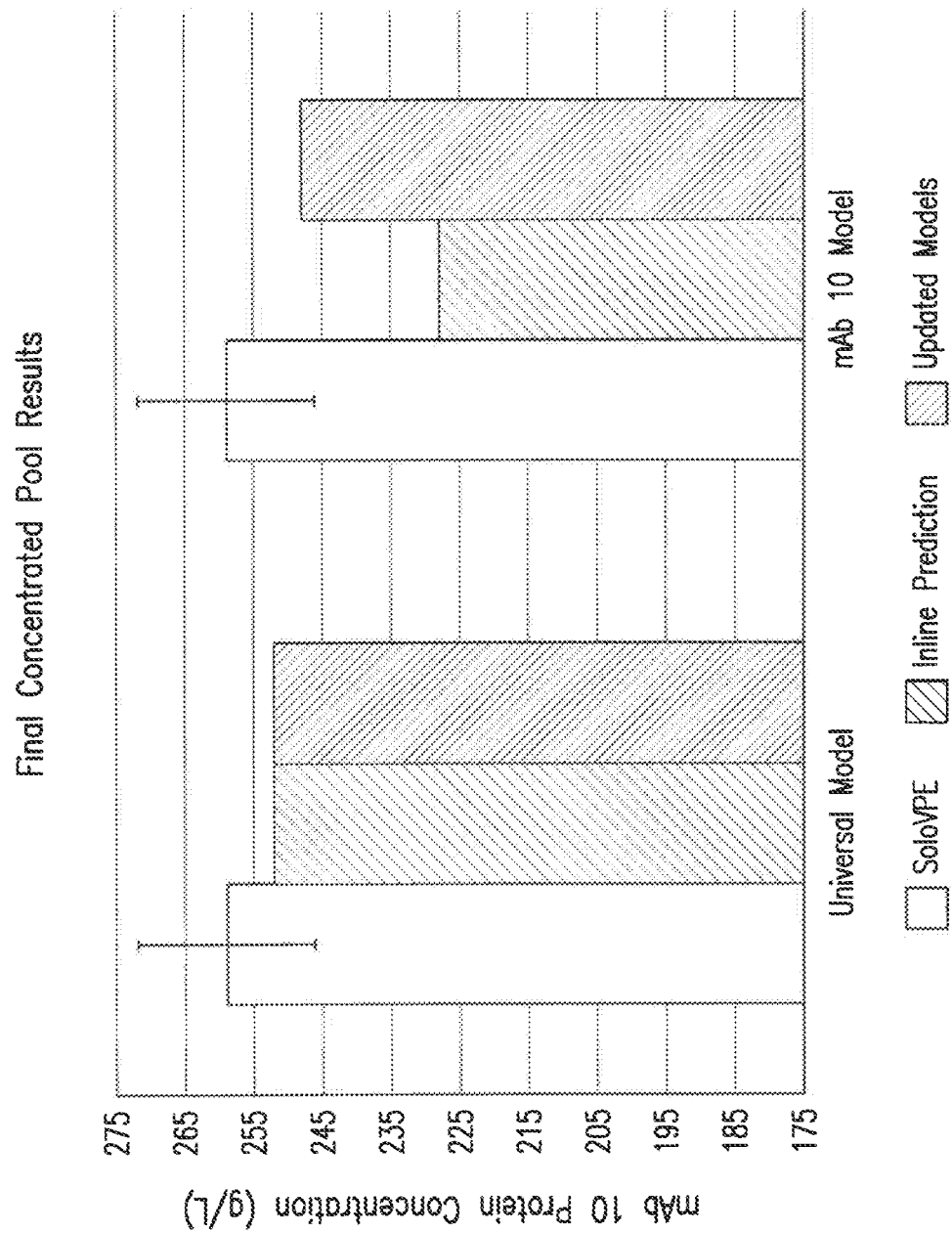
FIG. 7 is a bar graph showing protein concentration for mAb10 using the universal model or the mAb10 specific model for final concentrated pool (FCP) measurements. Protein concentrations are shown for inline real-time Raman predictions (bars with wide hatching), updated models (bars with narrow hatching), and SoloVPE (empty bar). The X axis represents experimental group and the Y axis represents protein concentration.

The model goal of ≤5% error was met for 2/4 updated models when the training set was included in the model predictions as shown in Table 3. Based on the notable differences such as the load source, laser and scale (bench scale vs. scale-up) during the preliminary experimentation at IOPS a second run was performed. Prior to the second experiment, a change was made to the 0-120 g/L mAb 10 specific model. All four regions were included using SNV pre-processing but the three regions, 977-1027 $cm^{-1}$, 1408-1485 $cm^{-1}$, and 1621-1711 $cm^{-1}$ additionally used $1^{st}$ derivative with 21 $cm^{-1}$ point smoothing. A summary of the compiled experimental results is summarized in Table 3. During the second experiment, the model goal of ≤5% error was met for 3/4 updated models when the training set was included in the model predictions as shown in Table 3. An additional observation made during data analysis was the load source being the main contributing factor to increased error. If the load sample is removed, the universal model error is reduced from 8.6% to 5.7%. In FIG. 7, the results for the inline predictions (real-time, bars with wide hatching) and updated models (bars with narrow hatching) for the final concentrated pool are shown comparing the protein concentration to the offline measurement of the SoloVPE (empty bars). The universal model inline and updated model had an error of 2.7% whereas the mAb 10 model inline and updated model was 12.0% and 4.2%, respectively for final concentrated pool. The increased error observed in the mAb 10 model can be attributed to limited data in the ~250 g/L range whereas the universal model has a larger data set. An additional contributing factor to the increased error is the inability of models to extrapolate outside the characterized range (i.e. >250 g/L in the mAb 10 model).

TABLE 3

Average Model Error for Protein Concentration Predictions in Scale Up

|  | IOPS Experiment # 1 | | IOPS Experiment # 2 | |
| --- | --- | --- | --- | --- |
|  | Inline | Updated | Inline | Updated[1] |
| Universal 0-120 g/L | 13.8% | 8.9% | 9.9% | 8.6% |
| Universal >120 g/L | 8.8% | 2.8% | 5.1% | 5.0% |
| mAb 11 0-120 g/L | 6.0% | 5.5% | 4.1% | 3.5% |
| mAb 11 >120 g/L | 12.0% | 1.5% | 8.8% | 3.6% |

[1]Removal of load sample reduces error; Universal (0-120 g/L): 8.6% to 5.7% and mAb11 (0-120 g/L): 3.5% to 2.7%

Example 3: Protein Concentration Model Scale-Up to Pilot Processing Equipment

Materials and Methods

During process development of commercially enabled processes, the UF/DF is characterized as unit operation following Quality by Design principles to understand critical process parameters as well as critical quality attributes. Raman and model development was included during mAb 11 development to enhance process understanding and propose a streamlined approach to model development. Refer to example 1 for method information for Raman data collection with the exception of scan time length which was adjusted from 10 seconds to 5 seconds. The developed mAb 11 model used SNV pre-processing for all four spectral regions but the three regions; 977-1027 $cm^{-1}$, 1408-1485 $cm^{-1}$, and 1621-1711 $cm^{-1}$ additionally used $1^{st}$ derivative with 21 $cm^{-1}$ point smoothing.

Figures 8A, 8B:
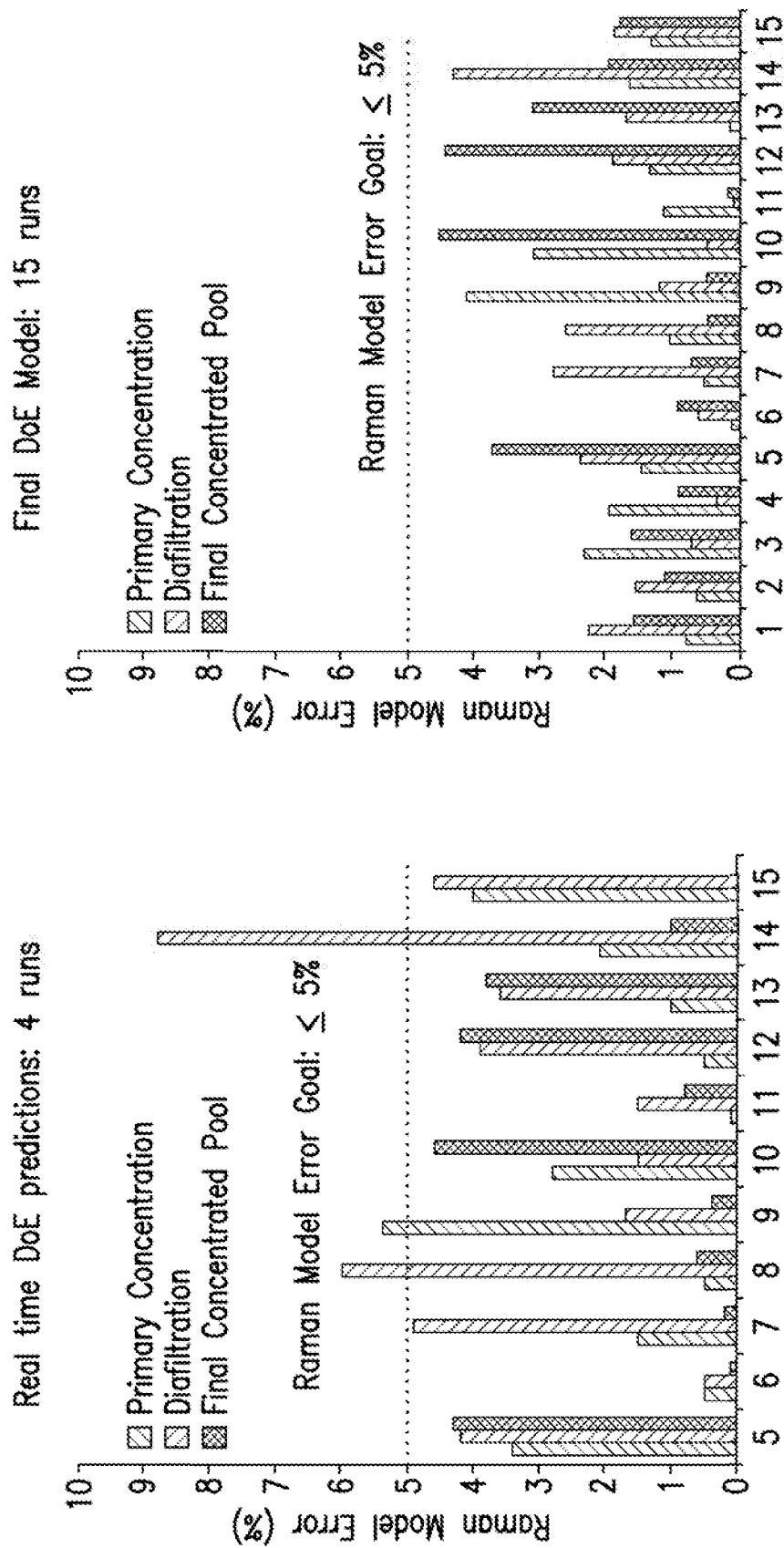
FIGS. 8A-8B are bar graphs showing Raman model error for bench scale DoE modeling for protein concentration.

Results:

The bench-scale model was generated using four DoE experiments and 4 spectral regions. FIG. 8A shows the Raman model error for real time predictions from four DoE experiments. FIG. 8B shows the Raman model error for 15 additional experiments using the bench scale model. mAb specific protein concentration models were generated for 0-120 g/L and >120 g/L with ≤5% error.

Figure 9A:
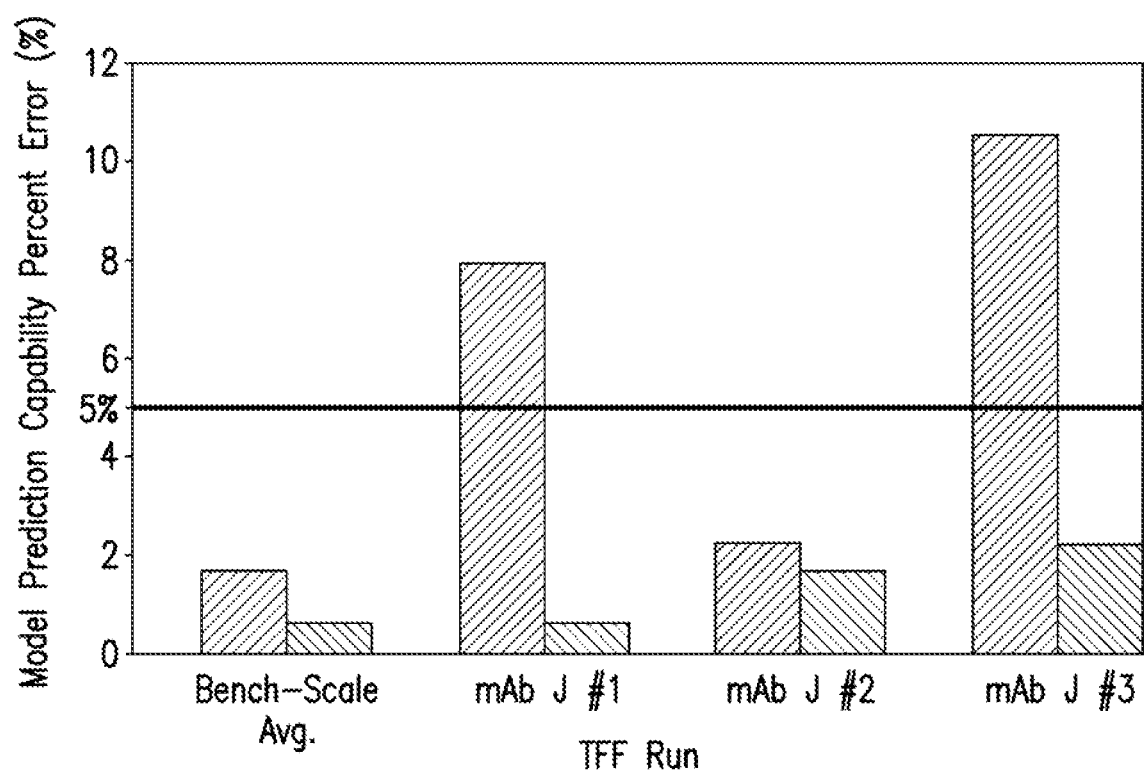
FIG. 9A is a bar graph showing model prediction capability percent error for model scale-up to pilot processing equipment for mAb11. Bench-scale model data is compared to bench-scale model date incorporating the pilot-scale data. The X-axis represents experimental groups and the Y-axis represents model prediction capability percent error (%).

Using bench-scale model (n=15), pilot-scale runs (n=3) have a prediction error of 0.6%-10.6% for mAb11 (FIG. 9A). Pilot-scale prediction error decreased to 0.6-2.2% when pilot-scale data was incorporated into the bench-scale model (n=18). Increased bench-scale model error is likely a result of temperature impact on Raman spectral shifts due to heat dissipation associated with scale-up equipment. Temperature will be a factor considered during future Raman development and model verification claims.

Figure 9B:
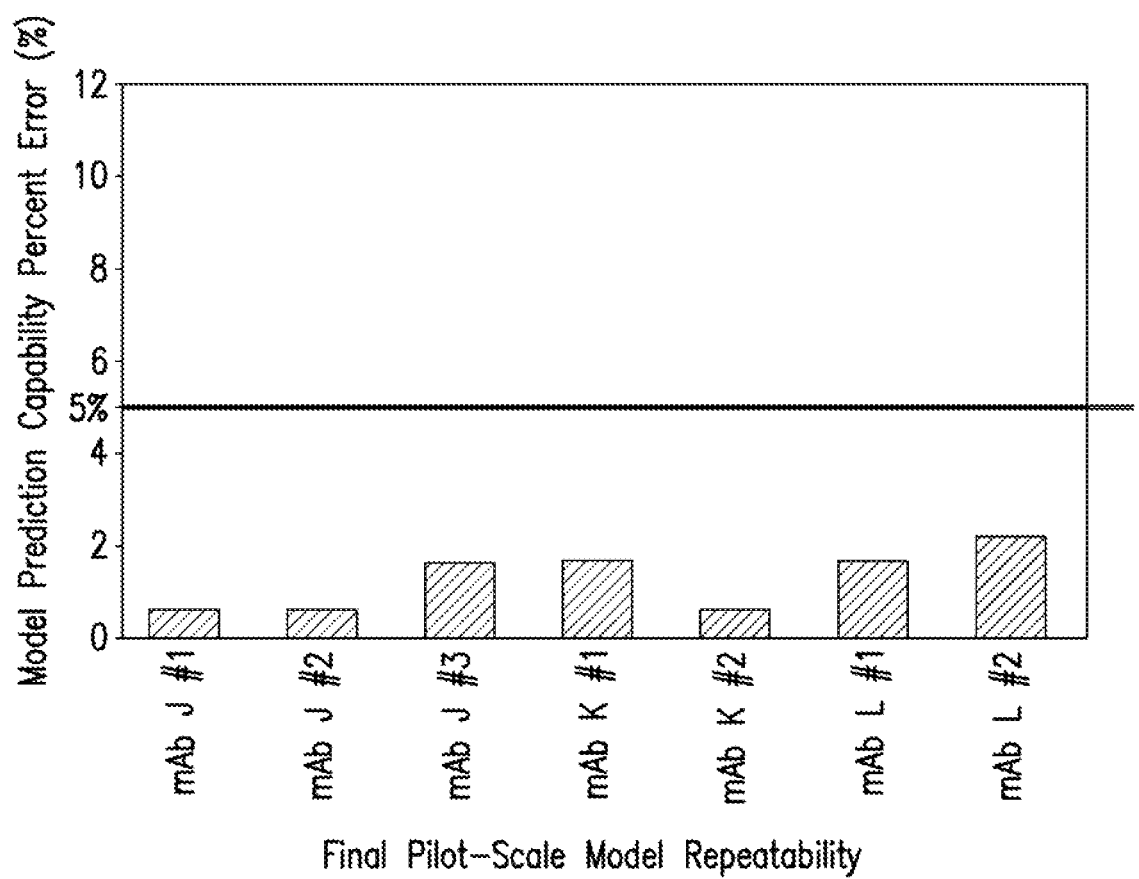
FIG. 9B is a bar graph showing model prediction capability for pilot-scale processing for various monoclonal antibodies. The X-axis represents experimental groups and the Y-axis represents model prediction capability percent error (%).

In seven pilot scale experiments with three different monoclonal antibodies (mAb J, mAb K, and mAb L) final model prediction error was 0.6-2.2%; well within the 5% goal (FIG. 9B).

Example 4: Use of Raman Models for Real-Time Concentration Determination Allowing Processing Decisions Materials and Methods:

Refer to example 3 for further information as the same protocol for Raman spectral collection and modeling was used for Raman automations. An automated control strategy was developed to use Raman spectral data to achieve final protein concentration targets. Using the generated predictive models, data was filtered, and was used to provide input to instrumentation on the UF/DF to terminate the unit operation upon achieving the protein concentration target. SoloVPE measurements were made in triplicate.

Figure 10A:
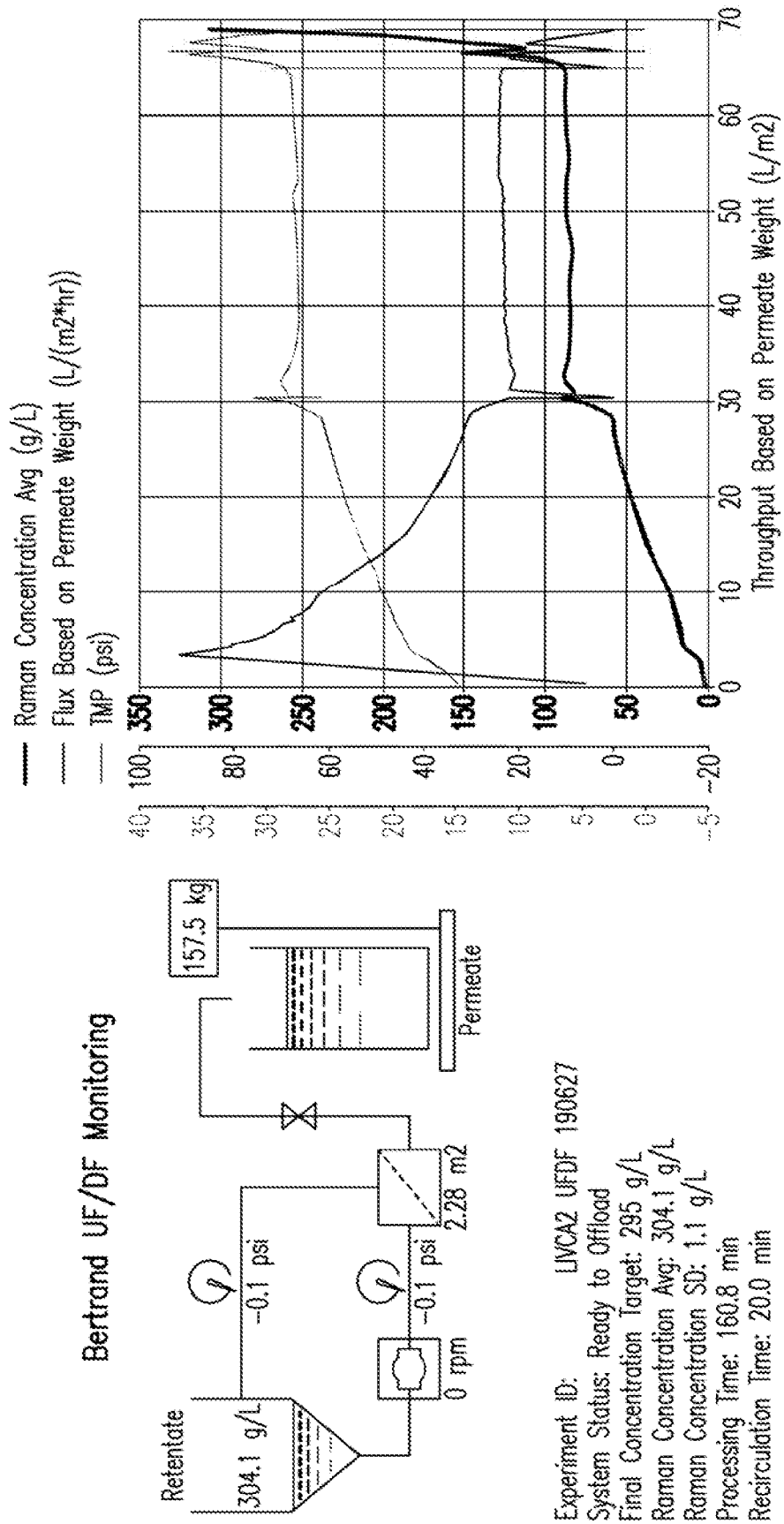
FIG. 10A is a schematic of an exemplary automated batch UF/DF with Raman feedback.
Figure 10B:
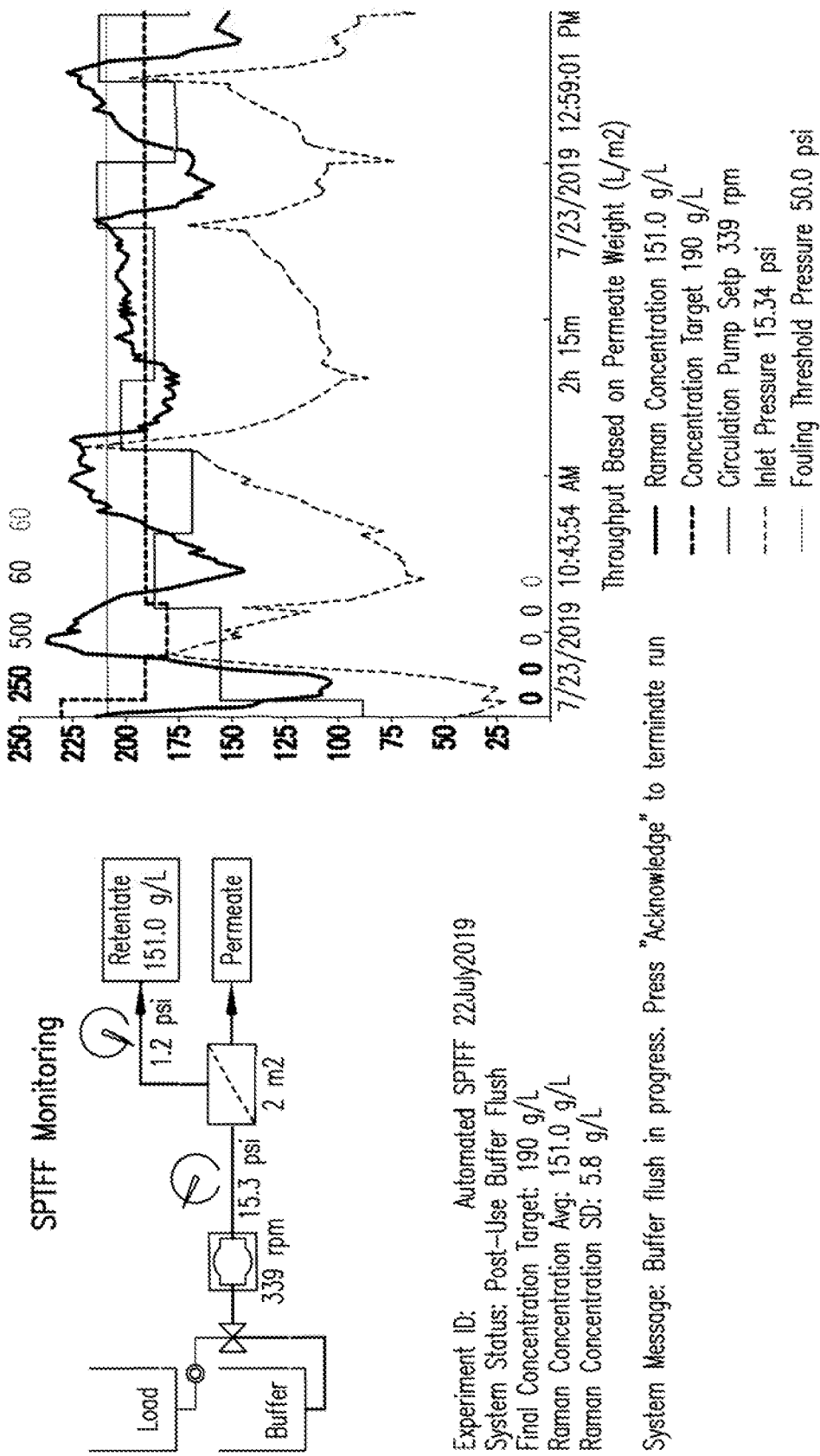
FIG. 10B is a schematic of an exemplary automated single pass TFF with Raman feedback.
Figure 11:
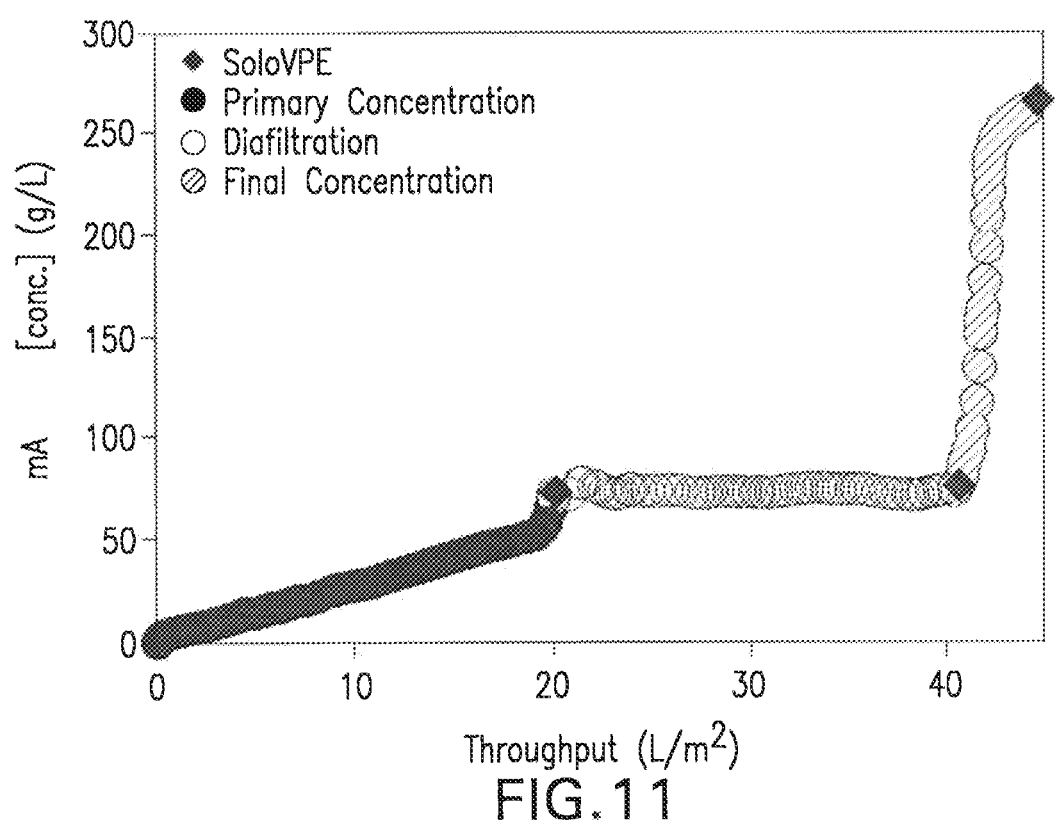
FIG. 11 is a graph showing mAb14 concentration over the course of UF/DF processing. The X-axis represents throughput ($L/m^2$) and the Y-axis represents mAb 14 concentration (g/L).

Results:

FIGS. 10A and 10B show exemplary screen setup for automated monitoring of batch UF/DF and single-pass TFF protein concentration. FIG. 11 shows that predictive modeling can be used to monitor real-time concentration of mAb14 throughout various processing steps and trigger the concentration unit operation to stop when a desired concentration target has been met. The final concentrated pool was predicted by Raman to be 260 g/L compared to the offline SoloVPE measurement of 262 g/L resulting in a 0.8% error meeting the ≤5% error goal. Raman is a suitable application to be used to make automated processing decisions verifying the desired protein concentration target is met.

Example 5: Proof of Concept for High Molecular Weight (HMW) Species Modeling in UF/DF Materials and Methods:

The data collection for the HMW species model included spectral data from Raman Rxn2 analyzers (Kaiser Optical Systems, Inc. Ann Arbor, Mich.) RamanRxn Probehead-758 (Kaiser Optical Systems, Inc. Ann Arbor, Mich.). Additionally, several different optics were used throughout development based on availability. Raman analyzers operating parameters were set to a 72 second scan time for 1 accumulation, repeated 25 times. Inline measurements were made throughout different points of UF/DF unit operation including primary concentration, diafiltration, and final concentration. The spectral range was 110-3415 $cm^{-1}$. The raw spectral data was pre-processed using SNV and additionally filtered using $1^{st}$ derivative with 21 $cm^{-1}$ smoothing. Offline HMW species measurements were determined using size-exclusion ultra performance liquid chromatography.

Results:

HMW species are another attribute that are deemed a preliminary critical quality attribute in protein purification.

Figure 12A:
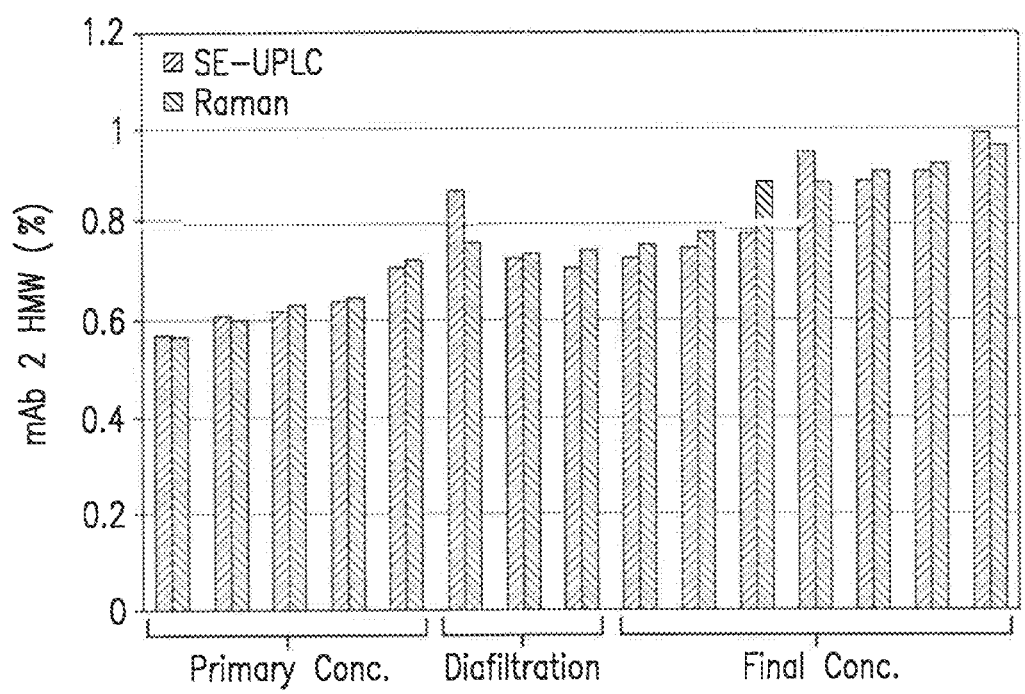
FIG. 12A is a bar graph showing the percent of high molecular weight (HMW) species in mAb2 during various steps of processing (primary concentration, diafiltration, final concentration) determined by either SE-UPLC or Raman modeling. The X-axis represents experimental group and the Y-axis represents mAb2 HMW percent (%).

Current technologies cannot monitor HMW species in real-time during processing. FIG. 12A shows that the disclosed Raman modeling method can be used to monitor HMW species during protein purification. HMW species predictions by Raman modeling were compared to measurements collected using SE-UPLC throughout purification (primary concentration, diafiltration, and final concentration). Raman modeling effectively predicted the percent of high molecular species in real-time during protein processing. The model was generated with an average error of 3.4%.

Example 6. Proof of Concept for High Molecular Weight (HMW) Species Modeling in Polishing Chromatography Materials and Methods:

The data collection for the HMW species model included spectral data from Raman Rxn2 analyzers (Kaiser Optical Systems, Inc. Ann Arbor, Mich.) utilizing MR-Probe-785. Raman analyzer operating parameters were set to either 10, 30, or 60 second scan times for 1 accumulations with 5 repetitive measurements. Offline measurements were made with anion exchange chromatography (AEX) pools with 6.2%-76.2% total HMW. The spectral ranges used for modeling and pre-processing techniques used are described in Table 4. Offline HMW species measurements were determined using size-exclusion ultra-performance liquid chromatography.

Figure 12B:
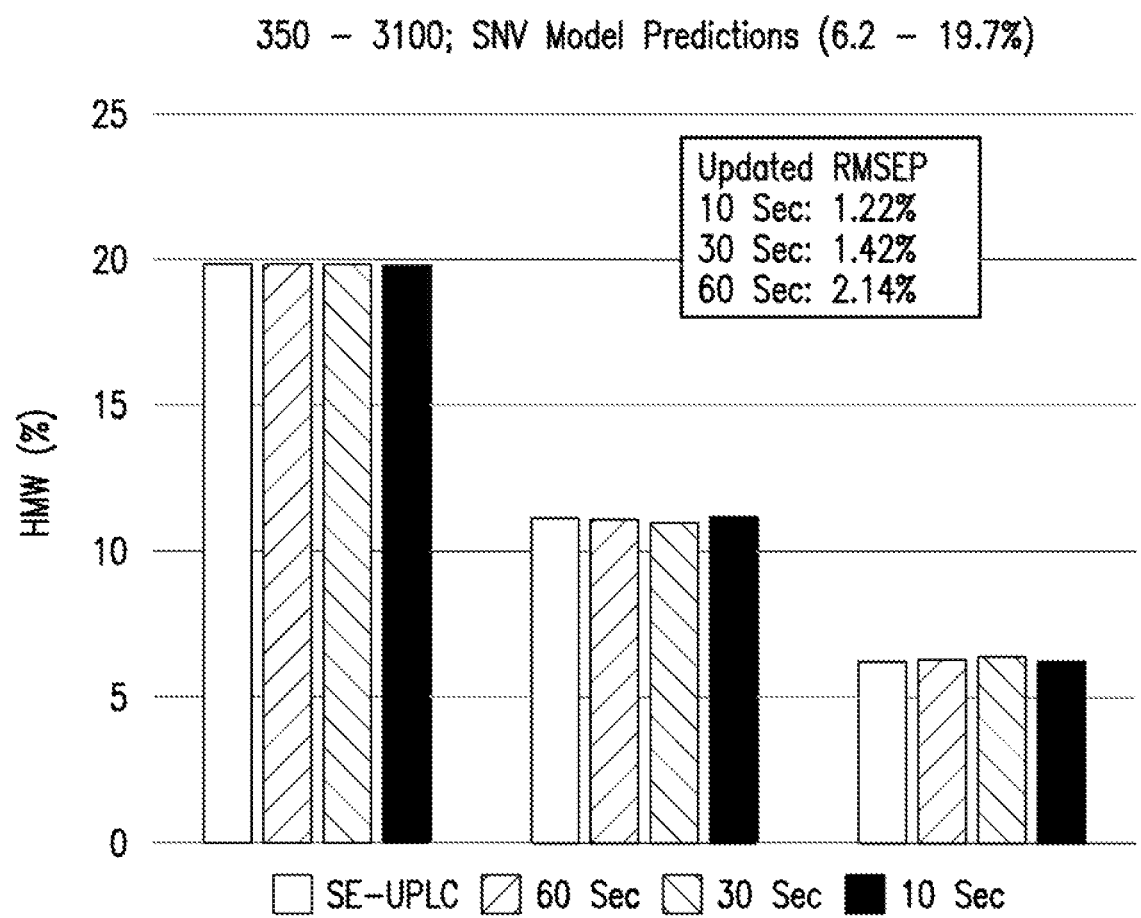
FIG. 12B is a bar graph showing the percent of high molecular weight (HMW) species predicted using various scan times (10 sec, 20 sec, 30 sec) for mAb 15. The X-axis represents experimental group and the Y-axis represents HMW percent (%).

Results:

The disclosed Raman modeling method can be used to monitor HMW species during polishing chromatography protein purification. HMW species predictions by Raman modeling were compared to measurements collected using SE-UPLC from the generated AEX pools. As summarized in Table 4, the RMSEP of the evaluated methods ranged from 3.2-7.6%. In FIG. 12B, a condensed data set of 6.2%-19.7% HMW was used to evaluate a model generated with a spectral region of 350-3100 $cm^{-1}$ and SNV pre-processing techniques. By reducing the HMW range, the RMSEP was reduced to 1.2%, 1.4%, and 2.1% for 10, 30, and 60 seconds respectively. Based on these results HMW content can be determined with Raman in AEX pools.

TABLE 4

HMW Model Predicted Error (RMSEP) for HMW content of 6.2%-76.2%.

| | 10 Sec. | 30 Sec. | 60 Sec. |
| --- | --- | --- | --- |
| 1550-1725 $cm^{-1}$ $1^{st}$ Der. | 7.62% | 5.31% | 3.21% |
| 350-3100 $cm^{-1}$ SNV | 3.48% | 3.37% | 4.63% |
| 990-1020, 1550-1725 $cm^{-1}$ $1^{st}$ Der. | 7.12% | 7.48% | 4.98% |

Example 7. Proof of Concept for Titer Modeling

Materials and Methods:

The training set model was 35 protein A flow through samples spiked with FCP (265 g/L) to achieve titers ranging from 0.36-9.8 g/L. The model was evaluated on diluted depth filtrate samples with titers ranging from 1.3-8.8 g/L. The data collection for the titer model included spectral data from Raman Rxn2 (Kaiser Optical Systems, Inc. Ann Arbor, Mich.) utilizing MR-Probe-785. An immersion probe was used in an offline fashion to generate spectral data with operating parameters set to a 20 second scan time for 1 accumulation, repeated 5 times. The spectral ranges were 977-1027, 1408-1485, 1621-1711, and 2823-3046 $cm^{-1}$. The raw spectral data was pre-processed using SNV and additionally filtered using $1^{st}$ derivative with 21 $cm^{-1}$ smoothing. Model characteristics are described in Table 5.

TABLE 5

Antibody Titer Model Characteristics.

| | |
| --- | --- |
| Spectral Regions ($cm^{-1}$) | 3046-2823, 1711-1621, 1485-1408, 1027-977 |
| Preprocessing techniques | $1^{st}$ derivative and SNV |
| Accumulations and Length | 5 × 20 seconds |
| Average Model Error | 25.7% |

Figure 13:
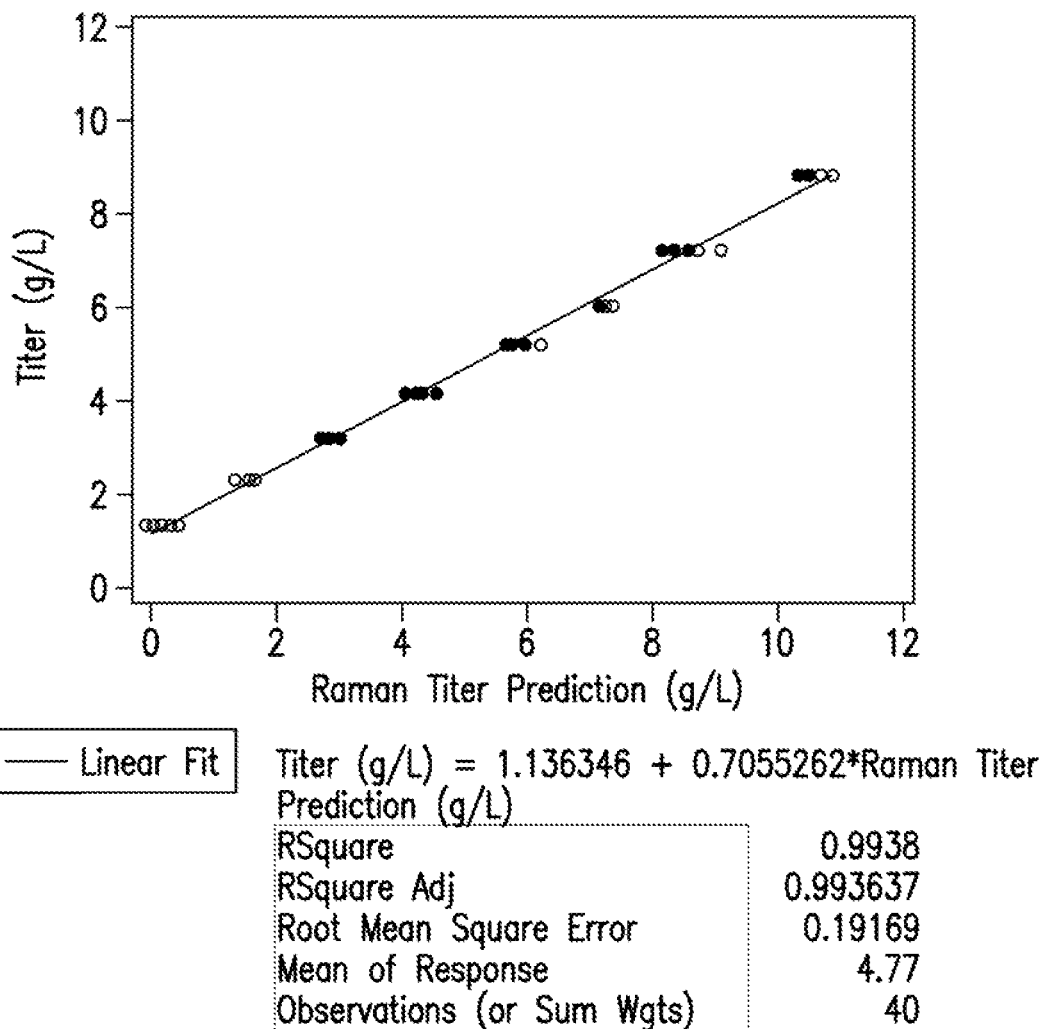
FIG. 13 is a dot plot showing actual titer (g/L) versus Raman predicted titer for monoclonal antibody samples from mAb 14. The X-axis represents Raman predicted titer and the Y-axis represents actual titer (g/L).

Results:

Antibody titer is a process attribute in protein purification that is needed to inform subsequent downstream purification unit operations including affinity column loading, production consistency, as well as in-process intermediate volume constraints. Inaccurate column loading can impact subsequent preliminary critical quality attributes hence the desire for a monitoring technique such as Raman spectroscopy. FIG. 13 shows actual antibody titer versus Raman predicted antibody titer for a monoclonal antibody. In this experiment, the model error was 26% which is higher than a desired goal of ≤5%. Increasing scan lengths as well as developing a model using diluted and non-diluted depth filtrate will reduce the model error.

Example 8: Raman Models for Buffer Excipient Measurements that Meet Current Orthogonal Assay Error of about 10%

Materials and Methods:

Data was collected from previous concentration model development runs for various antibodies. Refer to example 1 for method information for Raman data collection. Table 6 shows the model components for detecting histidine and arginine in the samples. The spectral regions were based on known histidine/arginine peaks (Zhu, et al., *Specirochim Acta A Mol Biomol Spectrosc*, 78(3):1187-1195 (2011)). Following initial model development of histidine and arginine, further model characterization was performed with mAb 14. Using a non-contact optic probe, Raman analyzer operating parameters were set to a 20 second scan time for 5 accumulations. The spectral range for histidine was 1200-1480 $cm^{-1}$ and for arginine 860-1470 $cm^{-1}$ were used. For both buffer excipients the raw spectral data was pre-processed using SNV and additionally filtered using $1^{st}$ derivative with 21 $cm^{-1}$ smoothing. Offline histidine and arginine species measurements were determined using an ultra-performance liquid chromatography (UPLC) amino acid quantification-based method.

Figure 14A:
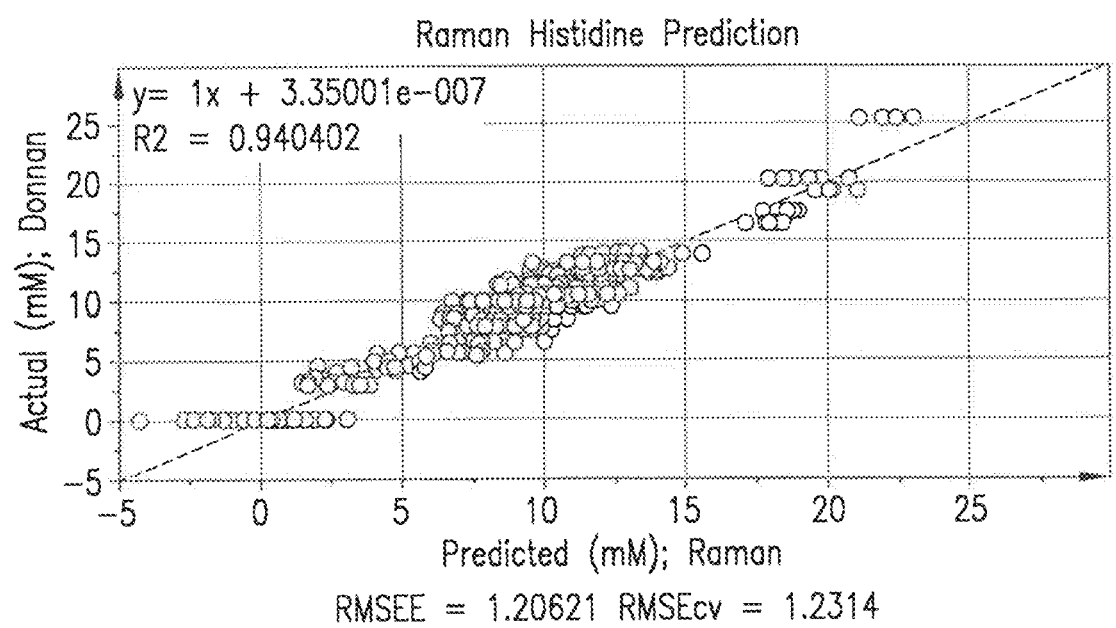
FIG. 14A is a scatter plot showing Raman histidine prediction in various monoclonal antibodies. The X-axis represents histidine concentration predicted by Raman modeling and the Y-axis represents actual histidine concentration determined by amino acid analysis.
Figure 14B:
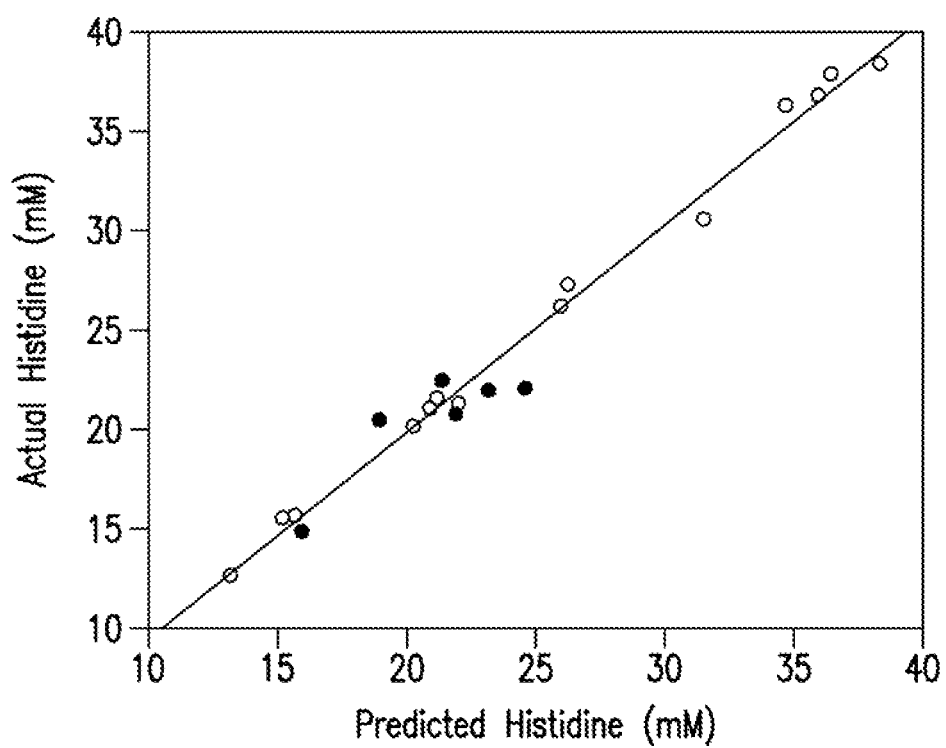
FIG. 14B is a dot plot showing actual histidine concentration versus Raman predicted histidine concentration for monoclonal antibody sample.
Figure 14C:
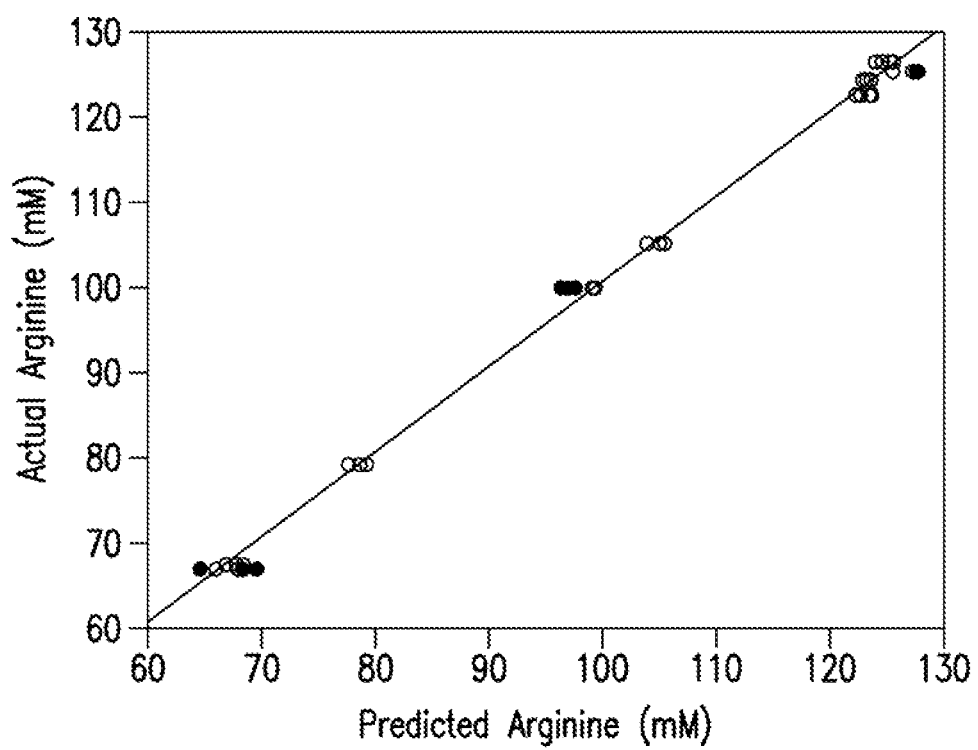
FIG. 14C is a dot plot showing actual arginine concentration versus Raman predicted arginine concentration for monoclonal antibody sample.

Results:

To determine if the disclosed Raman modeling method and system could be used to measure buffer excipients in a processed antibody sample, data collected from previous concentration model development runs were analyzed for histidine and arginine. Predicted values using Raman modeling were compared to values calculated based on the UPLC based amino acid method as can be seen in FIG. 14A. The predicted values and average model error for the preliminary histidine/arginine Raman modeling are presented in Table 6. In FIG. 14B a dot plot for predicted histidine versus actual histidine model is shown for mAb 14 with an average model error of 8.2% meeting the ≤10% goal for buffer excipients. The ≤10% goal is based on the current UPLC orthogonal method assay variability. In FIG. 14C a dot plot for predicted arginine versus actual arginine model is shown for mAb 14 with an average model error of 2.9% meeting the ≤10% goal.

This data shows that Raman modeling can be used to predict the levels of buffer excipients from in-process UF/DF and FCP material. Successful quantification of these excipients ensures that UF/DF provides a final concentrated pool that will enable subsequent formulation.

TABLE 6

Model components and data collected for histidine/arginine from universal concentration model (example 1) processing.

| | Histidine | Arginine |
|---|---|---|
| Spectral Region (cm$^{-1}$) | 1200-1480 | 970-1100, 1300-1500 |
| Preprocessing technique | 1$^{st}$ derivative and SNV | 1$^{st}$ derivative and SNV |
| R$^2$Y | 0.940 | 0.964 |
| Q$^2$ | 0.938 | 0.963 |
| RMSEP | 1.20 mM | 6.19 mM |
| Average Model Error | 10.4% | 7.39% |

Histidine Range: 0-25 mM; Arginine Range: 0-81 mM
SNV—Standard Normal Variate—mean centered and normalized
R$^2$—Percent of variation in the training set explained by the model, R$^2$ > 0.9
Q$^2$—Percent of variation in the training set predicted by the model during cross-validation, Q$^2$ > 0.8
(RMSEP) Root Mean Square Error Prediction Example 9: Raman Models for Drug-to-Antibody Ratio Measurements Materials and Methods:

DAR is a quality attribute that is monitored during development of antibody-drug conjugates (ADC), antibody-radionuclide conjugates (ARC), and general protein conjugates (potent steroids, non-cytotoxic payloads, etc.) to ensure consistent product quality and to facilitate subsequent labeling with payloads. Raman was evaluated as technology to monitor DAR levels which could then be used a control strategy for the reaction. Two different mAbs that were under development (mAb 1 and mAb 3) were assessed for DAR determination feasibility using Raman. Using a non-contact optic probe, Raman analyzer operating parameters were set to a 10 second scan time for 10 accumulations. The spectral range of 350-3100 cm$^{-1}$ was used with the raw spectral data pre-processed using SNV and additionally filtered using 2$^{nd}$ derivative with 21 cm$^{-1}$ smoothing. Table 7 shows the model components for determining DAR in the samples. Offline DAR measurements were determined using a UV spectroscopy-based method.

TABLE 7

Model components for drug-antibody ratio measurements.

| Model Name | REGN2810 UV-DAR | REGN910 UV-DAR |
|---|---|---|
| Y Range | 0.81-4.39 | 0.79-3.57 |
| Best Model | 2$^{nd}$ Derivative | 2$^{nd}$ Derivative |
| | R2Y = 0.788 | R2Y = 0.994 |
| | Q2 = 0.548 | Q2 = 0.776 |
| | RMSECV = 0.64 | RMSECV = 0.58 |

Figure 15A:
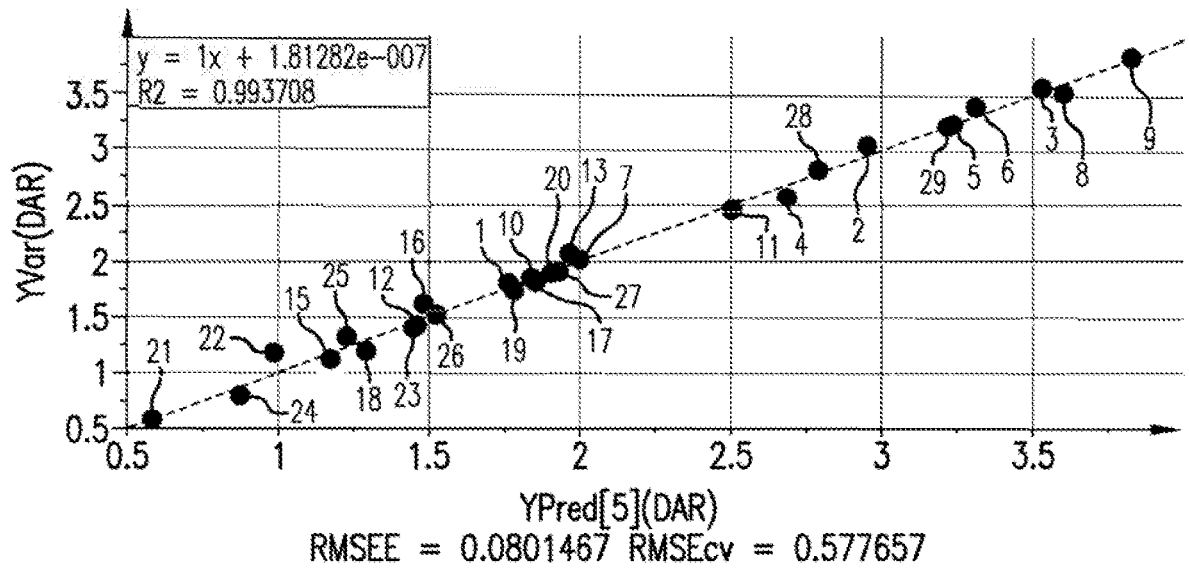
FIG. 15A is a scatter plot showing actual drug-antibody ratio (DAR) versus Raman predicted DAR for monoclonal antibody samples from mAb 3. The X-axis represents Raman predicted DAR and the Y-axis represents actual DAR determined by UV-spectroscopy.
Figure 15B:
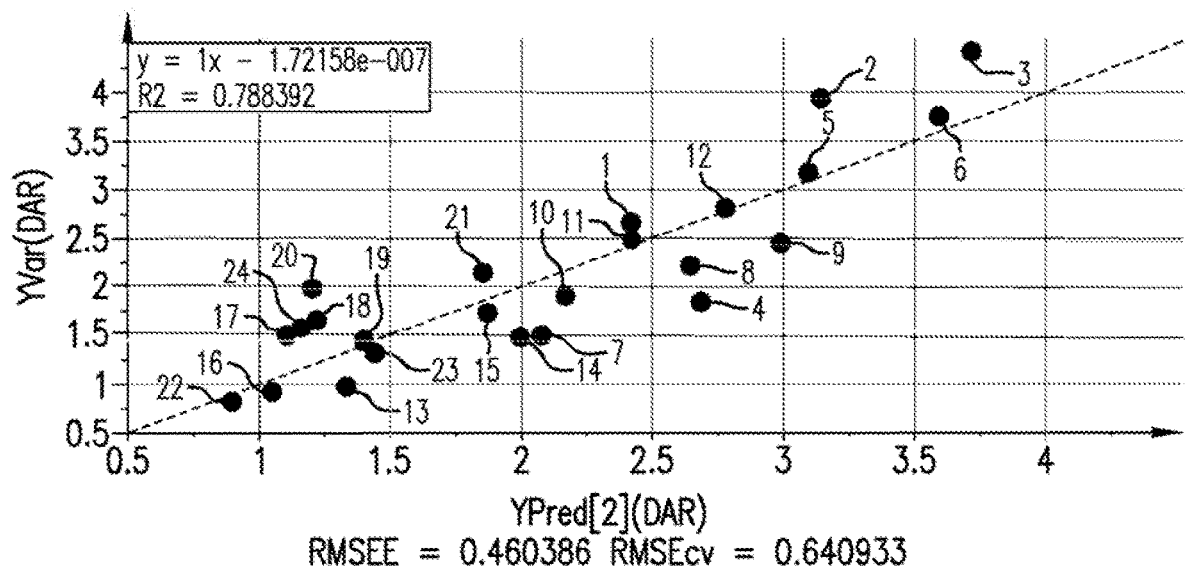
FIG. 15B is a scatter plot showing actual drug-antibody ratio (DAR) versus Raman predicted DAR for monoclonal antibody samples from mAb 1. The X-axis represents Raman predicted DAR and the Y-axis represents actual DAR.

Results:

FIGS. 15A-15B show that Raman modeling can be used to measure drug-to-antibody ratio for an iPET drug conjugates for mAb 1 and mAb 3. For both models the root mean square error of cross validation was 0.6 DAR. The current orthogonal UV based assay has variability associated with 0.3 DAR (one standard deviation). The initial Raman predication is within two standard deviations and suggests with further model refinement DAR can be successfully predicted with Raman.

While in the foregoing specification this invention has been described in relation to certain embodiments thereof, and many details have been put forth for the purpose of illustration, it will be apparent to those skilled in the art that the invention is susceptible to additional embodiments and that certain of the details described herein can be varied considerably without departing from the basic principles of the invention.

All references cited herein are incorporated by reference in their entirety. The present invention may be embodied in other specific forms without departing from the spirit or essential attributes thereof and, accordingly, reference should be made to the appended claims, rather than to the foregoing specification, as indicating the scope of the invention.

We claim:

1. A method of producing a concentrated protein purification intermediate comprising:
   providing a universal model produced using a plurality of protein purification intermediates;
   determining concentrations of a protein purification intermediate in-real time using in situ Raman spectroscopy with the universal model while concentrating the protein purification intermediate; and
   adjusting parameters of the concentrating step in-real time to obtain the concentrated protein purification intermediate and/or final concentrated pool, and
   wherein the concentration of the protein purification intermediate is at least 150 mg/mL.

2. The method of claim 1, wherein the concentrated protein product has a concentration of 150 mg/mL to 300 mg/mL.

3. The method of claim 1, wherein the protein purification intermediate is concentrated using ultrafiltration, buffer exchange, or both.

4. The method of claim 1, wherein the protein purification intermediate is harvested from a bioreactor, a fed-batch culture, or a continuous culture.

5. The method of claim 1, wherein determining the concentration of the protein purification intermediate occurs continuously or intermittently in real-time.

6. The method of claim 1, wherein the quantifying of protein concentration is performed in intervals from 30 seconds to 10 minutes, hourly, or daily.

7. The method of claim 1, wherein the protein purification intermediate is an antibody or antigen binding fragment thereof, a fusion protein, or a recombinant protein.

8. A method of producing a protein purification intermediate comprising:
   independently performing Raman Spectroscopy analysis on a plurality of protein purification intermediates to produce a universal model capable of quantifying any one of the plurality of protein purification intermediates;
   determining concentrations of a protein purification intermediate using in situ Raman spectroscopy with the universal model during concentration of the protein purification intermediate; and
   producing the concentrated protein purification intermediate when the concentrated protein purification intermediate reaches a predetermined concentration or the final concentrated pool target, and wherein the concentration of the protein purification intermediate is at least 150 mg/mL.

9. The method of claim 8, wherein the model is produced using Partial Least Squares Regression Analysis of raw spectral data and offline protein concentration data.

10. The method of claim 9, further comprising performing a normalization technique or point-smoothing on the Raman spectroscopy data.

11. The method of claim 10, wherein the normalization technique comprises standard normal variate.

12. The method of claim 10, wherein the point-smoothing comprises $1^{st}$ derivative with 21 cm$^{-1}$ smoothing.

13. The method of claim 8, wherein the model provides predicted protein concentration values for a plurality of protein purification intermediates with ≤5% error compared to off-line protein concentration values.

14. The method of claim 8, wherein the model provides predicted protein concentration values for a plurality of protein purification intermediates with ≤3% error compared to off-line protein concentration values.

15. The method of claim 8, wherein the concentrated protein purification intermediate has a concentration of 150 mg/mL to 300 mg/mL.

16. The method of 8, wherein the concentrated protein purification intermediate is concentrated using ultrafiltration, diafiltration, or both.

17. The method of claim 8, wherein the concentrated protein purification intermediate is harvested from a bioreactor, a fed-batch culture, or a continuous culture.

18. The method of claim 1, wherein determining the concentration of the protein purification intermediate occurs continuously or intermittently in real-time.

19. The method of claim 1, wherein the quantifying of protein concentration is performed in intervals from 30 seconds to 10 minutes, hourly, or daily.

20. The method of claim 8, wherein the protein purification intermediate is an antibody or antigen binding fragment thereof, a fusion protein, or a recombinant protein.

21. The protein purification intermediate produced according to claim 1.

22. A method of monitoring and controlling critical quality attributes in a protein purification intermediate during downstream protein purification processing comprising:
providing a universal model produced using a plurality of protein purification intermediates;
quantifying one or more critical quality attributes in the protein purification intermediate using in situ Raman spectroscopy; and
adjusting the one or more critical quality attributes in the protein purification intermediate to match predetermined critical quality attribute levels, and
wherein the concentration of the protein purification intermediate is at least 150 mg/mL.

23. The method of claim 22, wherein the critical quality attributes is selected from the group consisting of antibody titer, protein concentration, high molecular weight species, drug-antibody ratio and buffer excipients.

24. The method of claim 22, wherein the downstream protein purification processing is ultrafiltration/diafiltration.

25. A method for monitoring and controlling the levels of excipients in harvested cell culture fluid and/or protein purification intermediate during downstream purification comprising:
providing a universal model produced using a plurality of protein purification intermediates;
determining concentrations of the excipients in-real time using in situ Raman spectroscopy while purifying the cell culture fluid or protein purification intermediate; and
adjusting parameters of the purification step in-real time to obtain or maintain predetermined amounts of the excipients in the harvested cell culture fluid and/or protein purification intermediate, and
wherein the concentration of the protein purification intermediate is at least 150 mg/mL.

26. The method of claim 25, wherein the excipient comprises a buffer excipient.

27. The method of claim 25, wherein the excipient is selected from the group consisting of acetate, citrate, histidine, succinate, phosphate, hydroxymethylaminomethane (Tris), proline, arginine, sucrose, or combinations thereof.

28. The method of claim 25, wherein the excipient comprises a surfactant excipient.

29. The method of claim 28, wherein the surfactant excipient is selected from the group consisting of polysorbate 80, polysorbate 20, and poloxamer 188.

30. The method of claim 8, further comprising an excipient, wherein the excipient comprises polyethylene glycol and/or sucrose.

31. The method of claim 1, further comprising:
independently performing Raman Spectroscopy analysis on a plurality of protein purification intermediates to produce the universal model, wherein the universal model is capable of quantifying any one of the plurality of protein purification intermediates during primary concentration and/or diafiltration at a concentration between 0-120 g/L, and/or during final concentration at a concentration greater than 200 g/L in an ultrafiltration/diafiltration (UF/DF) system.

32. The method of claim 1, further comprising:
determining concentrations of an excipient in-real time using in situ Raman spectroscopy while purifying the harvested cell culture fluid and/or protein purification intermediate; and
adjusting parameters of the purification step in-real time to obtain or maintain predetermined amounts of the excipients in the harvested cell culture fluid and/or protein purification intermediate.

33. The method of claim 1, further comprising:
quantifying one or more critical quality attributes in the protein purification intermediate using in situ Raman spectroscopy; and
adjusting the one or more critical quality attributes in the protein purification intermediate to match predetermined critical quality attribute levels,
wherein the critical quality attributes is selected from the group consisting of antibody titer, protein concentration, high molecular weight species, drug-antibody ratio and buffer excipients.

34. The method of claim 1, wherein spectral data is collected at one or more wavenumber ranges selected from the group consisting of 977-1027 cm$^{-1}$, 1408-1485 cm$^{-1}$, 1621-1711 cm$^{-1}$, 2823-3046 cm$^{-1}$, and combinations thereof.

35. The method of claim 1, wherein the protein purification intermediate is a fusion protein.

36. The method of claim 1, wherein the protein purification intermediate comprises an extracellular domain of a cell surface receptor or a fragment thereof.

37. The method of claim 1, wherein the protein purification intermediate is a recombinant protein.

38. The method of claim 1, wherein the protein purification intermediate is a recombinant fusion protein.

39. The method of claim 1, wherein the protein purification intermediate comprises an Fc-fusion protein or fragment thereof.

40. The method of claim 1, wherein the protein purification intermediate comprises an anti-VEGF antibody or fragment thereof.

41. The method of claim 1, wherein the protein purification intermediate is an antibody or antigen binding fragment thereof.

* * * * *

UNITED STATES PATENT AND TRADEMARK OFFICE
CERTIFICATE OF CORRECTION

PATENT NO. : 11,358,984 B2
APPLICATION NO. : 16/550989
DATED : June 14, 2022
INVENTOR(S) : Passno et al.

It is certified that error appears in the above-identified patent and that said Letters Patent is hereby corrected as shown below:

On the Title Page

Item (73), please replace "Regeneran" with -- Regeneron --.

Signed and Sealed this
Second Day of August, 2022

Katherine Kelly Vidal
*Director of the United States Patent and Trademark Office*